US005567686A

United States Patent [19]
Grdina

[11] Patent Number: 5,567,686
[45] Date of Patent: Oct. 22, 1996

[54] METHOD FOR PROTECTION AGAINST GENOTOXIC MUTAGENESIS

[75] Inventor: David J. Grdina, Naperville, Ill.

[73] Assignee: Arch Development Corporation, Chicago, Ill.

[21] Appl. No.: 121,946

[22] Filed: Sep. 13, 1993

Related U.S. Application Data

[63] Continuation-in-part of Ser. No. 851,210, Mar. 13, 1992.
[51] Int. Cl.$^6$ ..................................................... A61K 31/66
[52] U.S. Cl. .......................... 514/43; 514/114; 514/555; 514/665
[58] Field of Search .............................. 514/43, 114, 555, 514/665

[56] References Cited

U.S. PATENT DOCUMENTS 3,892,824  7/1975  Piper et al. .

OTHER PUBLICATIONS

"A Survey of Compounds From the Antiradiation Drug Development Program of the U.S. Army Medical Research and Development Command," Walter Reed Army Institute of Research, Washington, DC, Sep. 1979.
Corn, B. W., Liber, H. L., and Little, J. B., "Differential Effects of Radical Scavengers on X–Ray–Induced Mutation and Cytotoxicity in Human Cells," *Radiation Research* 109, 100–108 (1987).
Nygaard, O. F. and Simic, M. G., excerpt from *Radioprotectors and Anticarcinogens*, 73–85, (1983).
Grdina, D. J., Dale, P. and Weichselbaum, R., "Protection Against AZT–Induced Mutagenesis at the HGPRT Locus in a Human Cell Line by WR–151326," submitted for publication in Jan. 1991 to *The International Journal of Radiation Oncology, Biology, Physics;* presented at the Seventh International Conference on Chemical Modifiers for Cancer Treatment, Clearwater, Florida, Feb. 2–5, 1991. (Supported in part by the U.S. Department of Energy, Office of Health and Environmental Research, under contract W–31–109–ENG–38; NIH/NCI grant CA–37435, U.S. Bioscience Inc. and the Center for Radiation Therapy.).
Milas, L., Hunter, N. and Stephens, L. C. and Peters, L. J., "Inhibition of Radiation Carcinogenesis in Mice by S–2(3–Aminopropylamino)–Methylphosphorothioic Acid," *Cancer Research,* vol. 44, 5567–5569, Dec. 1984. (Supported in part by grants CA–06294 and CA–16672, provided by the National Cancer Institute, Department of Health and Human Services.).
Grdina, D. J., Carnes, B. A., Grahn, D. and Sigdestad, C. P., "Protection Against Late Effects of Radiation by S–2–(3–Aminopropylamino)–Ethylphosphorothioic Acid," submitted to *Cancer Research,* vol. 51, 4125–4130 (1991). (Supported by the U.S. Department of Energy, under contract W–31–109–ENG–38; by NIH/NCI grant CA–37435 and by the Center for Radiation Therapy.).
Brown, J. M., "Sensitizers and Protectors and Radiotherapy," *Cancer,* 2222–22228, May 1 Supplement, 1985.

Constine, L. S., Zagars, G., Rubin, P. and Kligerman, M., "Protection by WR–2721 of Human Bone Marrow Function Following Irradiation," *Int. J. Radiation Oncology Biol. Phys.* vol. 12, 1505–1508, (1986).
Mahoney, F., "Summary Statement", Radiation Study Section, Feb. 1986.
Grdina, D. J., Nagy, B., Hill, C. K. and Sigdestad, C. P., "Protection Against Radiation–Induced Mutagenesis in V79 Cells by 2–[(Aminopropyl)amino] Ethanethiol Under Conditions of Acute Hypoxia," *Radiation Research* vol. 117, 251–258 (1989).
"Summary Statement," Radiation Study Section, Jan. 1989.
Maisin, J. R., Mattelin, G. and Lambiet–Collier, M., Chemical Protection Against the Long–Term Effects of a Single Whole–Body Exposure of Mice to Ionizing Radiation, *Radiation Research* 71, 119–131 (1977).
Kataoka, Y., Basic, I., Perrin, J. and Grdina, D. J., "Anti––mutagenic effects of radioprotector WR–2721 against fission–spectrum–neutrons and Co–gamma rays in mice," *Int. J. Radiation Oncology Biol Phys.,* vol. 61, 387–392 (1992). (Supported in part by the U.S. Department of Energy, Office of Health and Environmental Research, under contract W–31–109–ENG–38; NIH/NCI CA–37435 and the Center for Radiation Therapy in Chicago, Illinois).
Fry, R. J. M., "Radiation Carcinogenesis: Radioprotectors and Photosensitizers," *Radioprotectors and Anticarcinogens,* 417–436, (1983). (Supported by the Office of Health and Environmental Research, U.S. Department of Energy, under contract W–7405–eng–26 with the Union Carbide Corporation.).
Held, K. D., "Models for Thiol Protection of DNA in Cells," *Pharmac. Ther.,* vol. 39, 123–131, (1988). (Supported in part by PHS grants CA42167 awarded by the National Cancer Institute, DHHS).
Grdina, D. J. and Sigdestad, C. P., "Radiation Protectors: The Unexpected Benefits," *Drug Metabolism Reviews,* 20(1), 13–42, (1989). (Supported in part by the U.S. Department of Energy, Office of Health and Environmental Research, under contract W–31–103–ENG–38 and Public Health Service grant CA37435 awarded (D. J. G.) by the National Cancer Institute, Department of Human Services; and the U.S. Army Medical Research and Development Command, Fort Detrick, Maryland, under contracts DAMD17–86–C–6229 and DAMD17–C–7218 (C. P. S).
"1990 AACR Abstract Form" Temporary Abst. No. 247, of the paper Antimutagenic and Anticarcinogenic Effects of Aminothiols: Applications to the Clinic and Workplace. (Supported in part by U.S. Department of Energy contract W–31–109–ENG–38; NIH–NCI CA–37435 and the Center for Radiation Therapy in Chicago, Illinois).

(List continued on next page.)

*Primary Examiner*—Robert Gerstl
*Attorney, Agent, or Firm*—Reinhart, Boerner, Van Deuren, Norris & Rieselbach, S.C.

[57] ABSTRACT

A method and pharmaceutical for protecting against mutational damage in mammalian cells, irrespective of the nature of the mutagenic event or source of radiational or chemical insult or the like.

11 Claims, 26 Drawing Sheets

OTHER PUBLICATIONS

"Abstracts," 3rd International Conference on Anticarcinogenesis & Radiation Protection, Oct. 15–21, 1989.

"Abstracts," twenty–eighth Plenary Meeting of the Committee on Space Research, Jun. 26–Jul. 6, 1990.

Kataoka, Y., Basic, I., Perrin, J. and Grdina, D. J., "Antimutagenic effects of radioprotector WR–2721 against fission–spectrum neutrons $^{60}$Co gamma–rays in mice," *Int. J. Radiat. Biol.*, (1992). (Supported in part by the U.S. Department of Energy, Office of Health and Environmental Research, under contract W–31–109–ENG–38; NIH/NCI CA–37435 and the Center for Radiation Therapy in Chicago, Illinois).

Zhang, X., Lai, P. and Taylor, Y., "Differential Radioprotection of Cultured Human Diploud Fibroblasts and Fibrosarcoma Cells by WR1065," *International Journal of Radiation Oncology, Biology, Physics*, vol. 21, Supp. 1 (1991).

Corn, B. W., Liber, H. L. and Little, J. B., "Differential Effects of Radical Scavengers on X–Ray–Induced Mutations and Cytotoxicity in Human Cells," *Radiation Research* 109, 100–108, (1987).

Grdina, D. J., Kataoka, Y., Basic, I. and Perrin, J., "The radioprotector WR–2721 reduces neutron–induced mutations at the hypoxanthine–guanine phosphoribosyl transferase locus in mouse splenocytes and administered prior to or following irradiation," *Carcinogenesis*, 13, 811–814 (1992). (Supported in part by the U.S. Department of Energy, Office of Health and Environmental Research, under contract W–31–109–ENG–38; NIH/NCI CA–37435 and the Center for Radiation Therapy in Chicago, Illinois).

Grdina, D. J., Carnes, B. A., Grahn, D. and Sigdestad, C. P., "Protection against Late Effects of Radiation by S–2–(3–Aminopropylamino)–ethylphosphorothioic Acid," *Cancer Research* vol. 51, 4125–4130, Aug. 15, 1991. Supported by the U.S. Department of Energy under contract W–31–109–ENG–38, by NIH/NCI grant CA–37435 and by the Center for Radiation Therapy.).

Carnes, B. A and Grdina, D. J., "In vivo protection by the aminothiol WR–2721 against neutron–induced carcinogenesis," *Int. J. Radiat. Biol.* 61, 567–576 (1992). (Supported in part by the U.S. Department of Energy, Office of Health and Environmental Research, under contract W–31–109–ENG–38; NIH/NCI CA–37435 and the Center for Radiation Therapy in Chicago, Illinois).

Grdina, D. J., Wright, B. J. and Carnes, B. A., "Protection by WR–151327 against Late–Effect Damage from Fission–Spectrum Neutrons," *Radiation Research* 127, (1991). (Supported in part by the U.S. Department of Energy, Office of Health and Environmental Research, under contract W–31–109–ENG–38, the Center of Radiation Therapy and NIH–NCI grant CA–37435.).

Kataoka, Y., Basic, I., Perrin, J. and Grdina, D. J., "Anti––mutagenic effects of radioprotector WR–2721 against fission–spectrum–neutrons and $^{60}$Co gamma–rays in mice," *Int. J. Radiat. Biol.*, (1991). (Supported in part by the U.S. Department of Energy, Office of Health and Environmental Research, under contract W–31–109–ENG–38; NIH/NCI CA–37435 and the Center for Radiation Therapy in Chicago, Illinois).

Smoluk, G. D., Fahey, R. C., Calabro–Jones, P. M., Aguilera, J. A. and Ward, J. F., "Radioprotection of Cells in Culture by WR–2721 and Derivatives: Form the Drug Responsible for Protection," *Cancer Research* vol. 48, 3641–3647, Jul. 1, 1988. (Supported by grant CA–39582 from the National Cancer Institute).

Holwitt, E. A., Koda, E. and Swenberg, C. E., "Enhancement of Toposomerase I–Mediated Unwinding of Supercoiled DNA by the Radioprotector WR–33278," *Radiation Research* 124, 107–109, (1990).

Grdina, D. J., Dale, P. and Weichselbaum, R., "Protection Against AZT–Induced Mutagenesis at the HGPRT Locus in a Human Cell Line by WR–151326," submitted to *The International Journal of Radiation Oncology, Biology, Physics* for publication; presented at the Seventh International Conference on Chemical Modifiers of Cancer Treatment, Clearwater, Florida, Feb. 2–5, 1991. (Supported in part by the U.S. Department of Energy, Office of Health and Environmental Research, under contract W–31–109–ENG–38, NIH–NCI grant CA–37435, U.S. Bioscience Inc. and the Center for Radiation Therapy.).

Milas, L., Hunter, N., Stephens, L. C. and Peters, L. J., "Inhibition of Radiation Carcinogenesis in Mice by S–2–(3–Aminopropylamino)ethylphosphorothioic Acid," *Cancer Research*, vol. 44, 5567–5569, Dec. 1984. (Supported in part by grants CA–06294 and CA–16672 awarded by the National Cancer Institute, Department of Health and Human Services.).

Benova, D., "Antimutagenic Properties of WR 2721 and of a Radioprotective Mixture, ATP–AET–Serotonin, With Regard to X Ray Induced Reciprocal Translocations in Mouse Spermatogonia," *Int. J. Radiation Oncology Biol. Phys.*, vol. 13, 117–119 (1987).

Linnane, A. W., Zhang, C., Baumer, A. and Nagley, P., "Mitochondrial DNA Mutation and the Ageing Process: Bioenergy and Pharmacological Intervention," *Mutation Research*, vol. 275, 195–208 (1992).

"Preface: Aging of the 25th Chromosome," *Mutation Research*, vol. 275, 113–114 (1992).

Minnunni, M., Wolleb, U., Mueller, O., Pfeifer, A., Aeschbacher, H. U., "Natural Antioxidants as Inhibitors of Oxygen Species Induced Mutagenicity," *Mutation Research*, vol. 269, 193–200 (1992).

Holmes, G. E., Bernstein, C. and Bernstein H., "Oxidative and Other DNA Damages as the Basis of Aging: A Review," *Mutation Research*, vol. 275, 305–315 (1992).

Rosin, M. P. and Stich, H. F., "The Inhibitory Effect of Cysteine on the Mutagenic Activities of Several Carcinogens," *Mutation Research*, vol. 54, 73–81 (1978).

Wei, Y. H., "Mitochondrial DNA Alterations as Ageing–Associated Molecular Events," *Mutation Research*, vol. 275, 145–153 (1992).

Applegate, L. A., Lautler, D. and Tyrrell, R. M., "Endogenous Glutathoine Levels Modulate the Frequency of Both Spontaneous and Long Wavelength Ultraviolet Induced Mutations in Human Cells," *Carcinogenesis*, vol. 13, No. 9, 1557–1560 (1992).

Kirkwood, T. B. L. "DNA, mutations, and aging," *Mutation Research*, vol. 219, 1–7 (1989).

Nagy, B., Dale, P. and Grdina, D., "Protection Against cis–Diammine–dichloroplatinum Cytotoxicity and Mutagenicity In V79 Cells by 2–[(Aminopropyl)amino] ethanethiol," *Cancer Research*, vol. 46, 1132–1135 (Mar. 1986).

Nagy, B. and Grdina, D., "Protective Effects of 2-[(Aminopropyl)amino]Ethanethiol Against Bleomycin and Nitrogen Mustard–Induced Mutagenicity in V79 Cells," *The International Journal of Radiation Oncology, Biology, Physics*, vol. 12, 1475–1478 (Aug. 1986).

Grdina, D. J. and Meechan, P. J., "Effects of the Radioprotector WR–1065 on Normal Human Skin Fibroblast Cells in Culture", Radiation Research Meeting, Mar. 19–25, 1993.

Grdina, D. J., Constantinou, A. and Shigematsu, N., "Inhibition of Topoisomerase II Activity in Repair–Proficient CHO K1 Cells by WR–1065", Radiation Research Meeting, Mar. 19–25, 1993.

Kataoka, Y., Shigematsu, N., O'Conner, T., Ward, W. and Grdina, D. J., "Captopril Protects Against Mutagenesis at the HPRT Locus in $^{60}$Co y–Ray–Irradiated CHO–AA8 Cells", Radiation Research Meeting, Mar. 19–25, 1993.

Van Beek, M. Doak, R., Sigdestad, C., and Grdina, D. J., "Pathological Effects of the Radiation Protector WR–151327 in Mice", *Radiation Research*, 124, 79–84 (1990).

Grdina, D. J., Nagy, B., Hill, C., Wells, R. and Peraino, C., "The radioprotector WR–1065 reduces radiation–induced mutations at the hypoxanthing–guanine phophoribosyl transferase locus in V79 cells", *Carcinogenesis*, vol. 6, No. 6, pp. 929–931, 1985.

WR-33278

SPERMINE

3-[(2-mercaptoethyl) amino] proplonamide p-toluenesulfonate (WR-2529)

$$N_2NCCH_2 \ NH \ CH_2 \ CH_2-SH \ (CH_3 \ O \ SO_3H)$$
with O double-bonded to the C S-1-(2-hydroxy-3-amino) propyl phosphorothioic acid (WR-77913)
$$N_2N \ CH_2 \ CH \ (OH) \ CH_2 \ SPO_3 \ H_2$$

2-[3-(methylamino) propylamino] ethanethiol (WR-255591)
$$CH_3 \ NH(CH_2)_3 \ NH \ CH_2 \ CH_2 \ SH$$

S-1-(aminoethyl) phosphorothioic acid (WR-638)
$$H_2N \ CH_2 \ CH_2 \ SPO_3 \ H_2$$

S-[2-(3-methylaminopropyl) aminoethyl] phosphorothioate acid (WR-3689)
$$CH_3NH \ (CH_2)_3 \ NHCH_2 \ CH_2 \ SPO_3 \ H_2$$

S-2-(4-aminobutylamino) ethylphosphorothioic acid (WR-2822)
$$H_2N \ (CH_2)_4 \ NH \ CH_2 \ CH_2 \ CH_2 \ SPO_3 \ H_2$$

FIG. 7A

S-2-(5-aminopentylamino) ethyl phosphorothioic acid  (WR-2823)
$H_2N\,(CH_2)_5\,NH\,CH_2\,CH_2\,SPO_3\,H_2$ 1-[3-(3-aminopropyl) thiazolidin-2-Yl]-D-gluco-1,2,3,4,5- (WR-255709)
pentane-pentol dehydrochloride S-2-(3-aminopropylamino) ethylphosphorothioic acid  (WR-2721)
$NH_2(CH_2)_3\,NH\,CH_2\,CH_2\,S\,PO_3\,H_2$ 2-[(aminopropyl) amino] ethanethiol  (WR-1065)
$NH_2(CH_2)_3\,NH\,CH_2\,CH_2\,SH$

| CELL TYPE | WR-1065 | γ-RAY | TOPO I (UNITS/μg PROTEIN)[a] | TOPO II α |
|---|---|---|---|---|
| K1 | − | − | 112 ± 20 | 59 ± 14 |
| K1 | + | − | 97 ± 28 | 16 ± 3[b] |
| K1 | − | + | 82 ± 22 | 53 ± 28 |
| K1 | + | + | 96 ± 28 | 36 ± 13[c] |

[a] MEAN ± S.D. OF FOUR EXPERIMENTS
[b] SIGNIFICANT DIFFERENCE AT p = 0.019
[c] SUGGESTIVE DIFFERENCE AT p = 0.061

Fig. 10A

| CELL TYPE | WR-1065 | γ-RAY | 100 × AREA[a] |
|---|---|---|---|
| K1 | − | − | 167 ± 55 |
| K1 | + | − | 179 ± 49 |
| K1 | − | + | 219 ± 21 |
| K1 | + | + | 163 ± 39 |

[a] MEAN ± S.D. OF AT LEAST THREE EXPERIMENTS

Fig. 10B

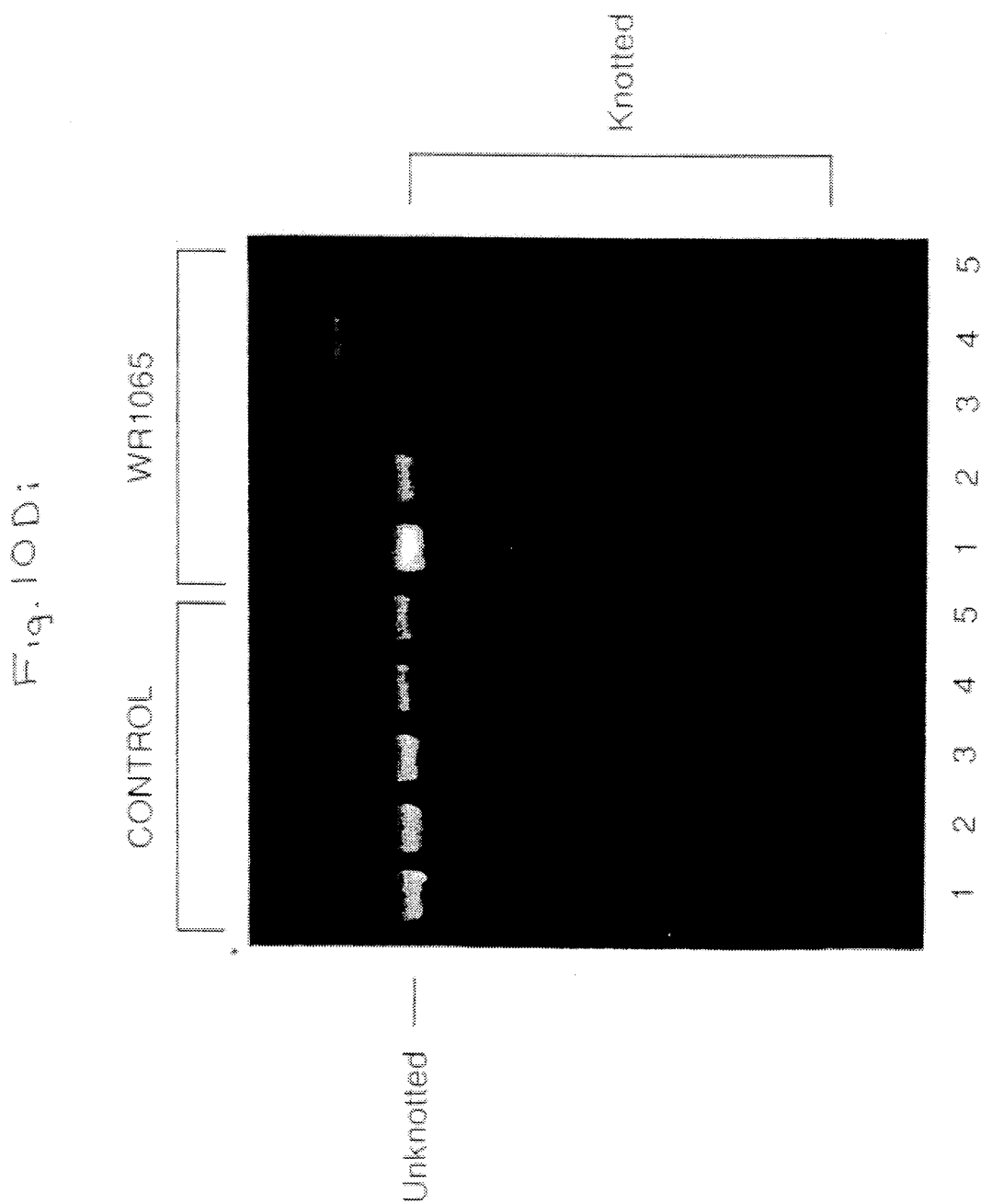

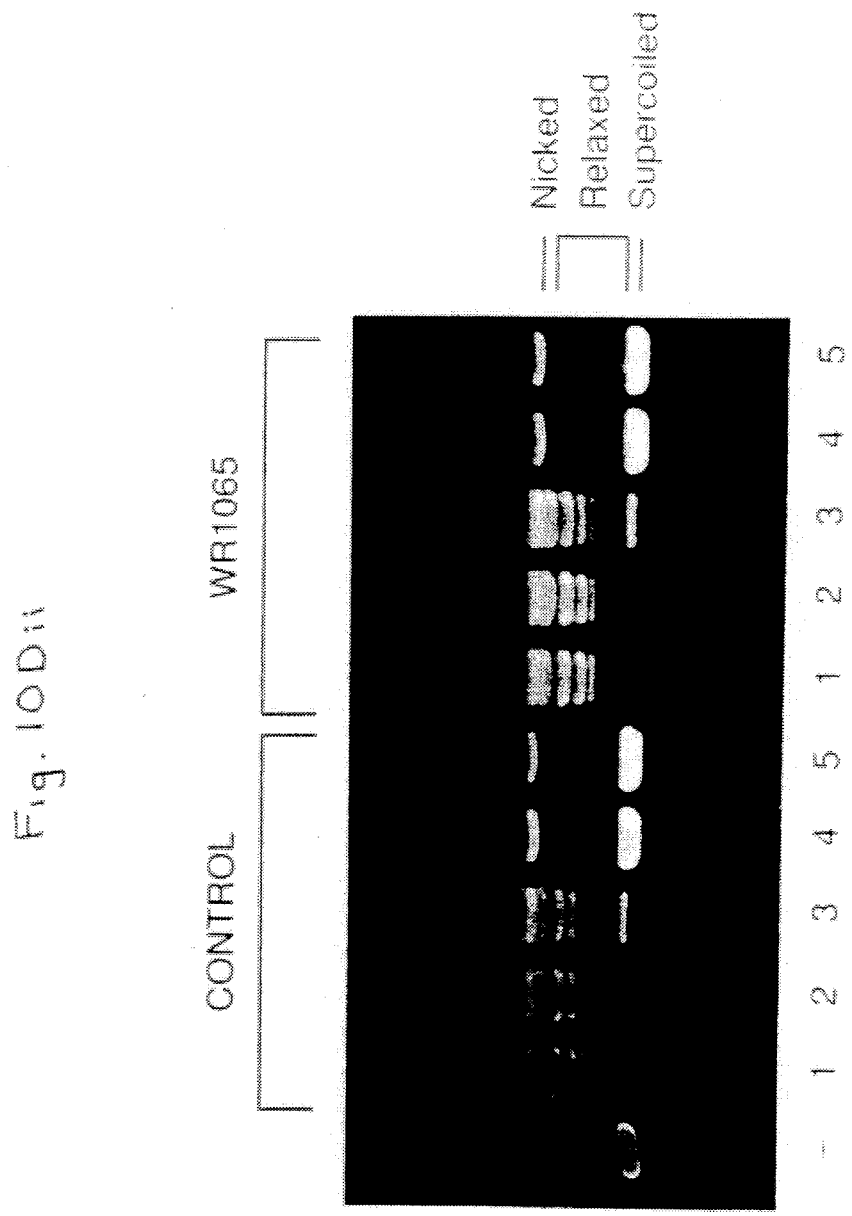

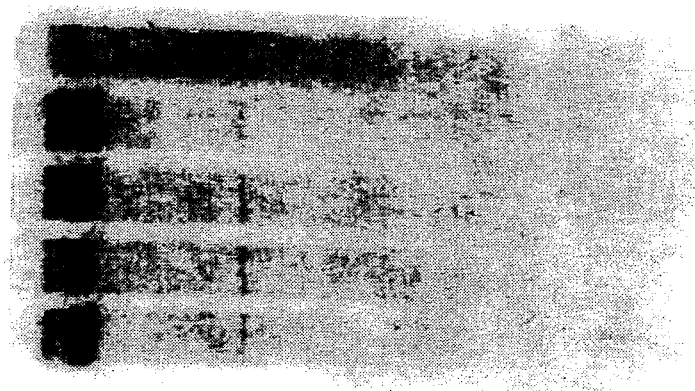
Fig. 10Gii

METHOD FOR PROTECTION AGAINST GENOTOXIC MUTAGENESIS

This is a continuation-in-part of copending application Ser. No. 07/851,210 filed on Mar. 13, 1992.

The present invention is generally directed to a method for protecting against genomic destabilization in mammalian cells from chemical or radiational mutagenic events and the like. More particularly, the invention is concerned with mutation reduction through use of S-ω(ω-aminoalkylamino)alkyl dihydrogen phosphorothioates and their corresponding metabolites.

Classic somatic mutation models of aging hold that the aging function is the result of an accumulation, over time, of mutational events in nuclear DNA; see, Kirkwood, *Mutat. Res.*, Vol. 219, pp. 1–7 (1988), and/or mitochondrial DNA (mtDNA); see Linnane, et al, *Mutat. Res.* Vol. 275, pp. 195–208 (1992). With respect to the contribution of mtDNA mutations to the phenotype of aging, the central premise is that accumulation of random mutations in the cellular population is a major contributor to the gradual loss of cellular bioenergy capacity within tissues and organs, and that general senescence and diseases of aging are associated therewith.

Deletions of mtDNA were previously thought to occur only in individuals with neuromuscular disease. However, one particular deletion (mtDNA$^{4977}$) accumulates with age primarily in non-dividing muscle and brain cells. Consistent with the contribution of mtDNA to aging is that the genome of this organelle appears especially sensitive to endogenous and environmental mutagens, given the lack of protective histones. It is postulated that deleted mtDNA and DNA fragments may be further degraded or translocated from the mitochondria to the nucleus, a route substantiated by observations of inserted mtDNA sequences into nuclear DNA. Thus, it is speculated that fragments of migrating mtDNA may change the information content and expression of certain nuclear genes. Such genomic destabilization may thereby promote aging and carcinogenic processes.

Age-dependent genomic alterations have also been observed in the nuclear DNA of dividing cells. Genomic destabilization is observed through the incidence of tumorigenic mutations that strike genes involved in the control of cell proliferation, i.e., the protooncogenes and tumor suppressor genes. See, *Mutat. Res.*, Vol. 275, pp. 113–114 (1992). The principle of chemoprevention is the reduction in incidence of mutagenic events, thus preventing the onset of the carcinogenic process.

Mutagenesis, whether mitochondrial or nuclear in nature, is widely thought to be the result of the effect of reduced, reactive oxygen species and associated free radicals. Mitochondrial DNA is continually exposed to such oxy-radicals. The age-dependent decline in the capability and capacity of mitochondria to dispose of these reactive species eventually render mtDNA more vulnerable to mutagenic events during the aging process. Through a variety of proposed mechanisms, free radicals, whether generated by radiation or during normal cell respiration, have been shown in the prior art to induce a multitude of different DNA lesions in mammalian tissues, as well as in bacteria, and have also been implicated in carcinogenic processes. See, *Mutat. Res.*, Vol. 269, pp. 193–200 (1992).

Reactive oxygen species and related free radicals may be generated with equal effect through a variety of exogenous (environmental) or endogenous agents, the result of chemical or radiational insult and the like. Regardless of the origin or cellular mechanism, these mutagenic events are expressed through genome destabilization and eventual mutagenesis.

Ionizing radiation is often employed in laboratory studies as a surrogate for other various environmental mutagenic agents. The propriety of such an assumption has been demonstrated in vitro using stock cultures of selected hamster cell lines which exhibited identical mutagenesis at the hypoxanthine-guanine phosphoribosyl transferase (HPRT) locus exposed to either ionizing radiation or cis-diaminedichloroplatinum (II). See, Grdina et al, *Cancer Research*, Vol. 46, pp. 1132–1135 (1986); and Grdina et al, *Int. J. Radiation Oncology Biol. Phys.*, Vol. 12, pp. 1475–1478 (1986).

The prior art is concerned with protecting against the genotoxic effects of radiation by the S-ω-(ω-aminoalkylamino)alkyl dihydrogen phosphorothioates and has focused on the pre-irradiation effect of dosages on amelioration of radiation's lethal effects with no appreciation for the antimutagenic, but only mutagenic effects. In prior art uses, it was required to administer maximum tolerated levels of the drugs prior to radiation exposure. Such requirements have limited the effectiveness of these agents because, when administered at the required maximum tolerated dose, they are debilitating causing fever, chills, rash, hypotension, nausea and vomiting. It is conventionally accepted that the drugs must be administered prior to radiation exposure which heretofore has precluded their use for individuals accidentally exposed to radiation.

Since 1949, the status of the prior art dictates that, in order for the radioprotective drug to be effective, it must be present before radiation exposure. The conventional understanding is also that the disulfide form of radioprotectors is incapable of providing protection. In drugs such as WR-2721 the level of protection is proportional to the amount of the drug administered. The prior art also teaches there are potential mutational properties of these agents which must be avoided. In particular, it has been suggested that one such agent in this class of phosphorothioates identified as S-2(3-aminopropylamino)ethyl phosphorothioic acid (also known as "WR-2721"), by way of intracellular reactions, can lead to the conversion of cytosine moieties in DNA to uracil. The result of use of WR-2721 can then be a mutagenic reaction in normal tissue.

These above enumerated concerns, along with conventional wisdom existing since as long ago as 1949, have prevailed and have discouraged investigation into the potential of phosphorothioates and related aminothiol compounds as chemopreventative agents.

Radioprotection is distinguished from chemoprevention in that the former refers to protection against cell killing by irradiation and the latter refers to protection against mutagenic and related carcinogenic processes. Phosphorothioates and related compounds, when employed as radioprotectors, are operationally defined as materials which can protect against genotoxic damage induced by known mutagens and carcinogens occurring as a result of ionizing radiation administered after ingestion of the chemical agent or drugs. The accepted protective mechanisms of action of these drugs include: the scavenging of free radicals produced as a result of the radiolysis of cellular water (presumably, free radical damage to DNA); the repair of chemical lesions via hydrogen atom donation; and the induction of cellular hypoxia. The deleterious effects of radiation occur via the deposition of energy in less than $10^{12}$ sec, while the relaxation of ionizations and excitations occur in less than $10^2$ sec. Damage to DNA, which leads to cell lethality, is completed between $10^7$ and $10^3$ sec. These models are consistent with the failure to demonstrate protection against cell lethality by the phosphorothioates and related aminothiols when they are administered immediately following radiation exposure.

In 1985 it was reported that a free thiol designated 2-[(aminopropyl)amino]ethanethiol could protect against somatic mutations at the hypoxanthine-guanine phosphoribosyl transferase locus in cultured rodent cells (designated V79), even if it were administered 3 h following irradiation. These in vitro results relating to post irradiation exposure and protection by this agent against mutagenesis were extended in 1989 to include protection against fission-spectrum neutrons. The extreme toxicity of this agent precluded its testing under in vivo conditions to ascertain the actual anti-mutagenic effect in a mammal. In 1987 the drug cysteamine was tested as an antimutagen, but no protective effects were observed unless it was present during irradiation (administered prior to).

The problem of genome instability and subsequent mutagenesis is associated both with endogenous and environmental mutagenic agents, including cosmic radiation, ultra violet light, radiation from nuclear reactors and war-released materials, and radiation from diagnostic and therapeutic sources. The development of mutations and related carcinogenic and aging processes arising from these and like radiation sources are well-documented and proven to be major health risks to the population as a whole, as well as to high-risk groups employed in the nuclear power industry, military, and patients receiving diagnostic and therapeutic radiation treatments. Likewise, mutagenic events originate from a variety of chemical and chemotherapeutic agents.

There exists a need for a method for protecting against mutations irrespective of the source of mutagenic event or insult which will be amenable to pre- and/or post-radiation administration and which will be effective at relatively low non-toxic concentrations so as to allow use in mammals and also allow for multiple, as well as single, administrations.

Accordingly, it is an object of the present invention to provide a novel method and substance for reducing mutations of mammal cells, including humans, exposed to radiation or chemical insult and like mutagenic events.

It is another object of this invention to provide a method of and compositions for protection against mutagenesis, irrespective of the source of mutagenic event or insult, such that genome stabilization is provided and that aging and carcinogenic processes are inhibited.

It is another object of the invention to provide an improved method for use of aminothiols and associated metabolites which diminish mutation of both cancerous and normal cells exposed to radiation or chemotherapy and the like, whether administered before or after therapy.

It is an additional object of the invention to provide a method using S-ω-(ω-aminoalkylamino)alkyl dihydrogen phosphorothioates to protect against initial mutagenic events irrespective of their source or nature and promote genome stabilization, such that subsequent mutagenesis and loss of genetic information is prevented.

It is still another object of the invention to provide a class of aminothiol agents which metabolize in vivo to produce free sulfhydryl groups and disulfides for protection against mutagenesis in mammalian cells.

It is a further object of the invention to provide a therapeutic route by which an aminothiol and/or aminodisulfide metabolite of a phosphorothioate agent is utilized to provide protection against mutagenic events and subsequent mutagenesis.

It is another object of this invention to provide a method for use of an antimutagenic agent to modulate cellular enzymatic processes, stabilize genomic material, prevent loss of cell function and genetic information, and increase the efficiency of and time available for cell repair processes.

It is still another object of this invention to provide a method for use in vivo of an antimutagenic agent to enhance the fidelity of mutational repair through delay of cell cycle progression or related cellular mechanisms.

It is a further object of this invention to provide a method for in vivo use of compositions which are both reactive toward the deleterious formation of free radical species by exogenous or endogenous sources and mitigate the mutational damage induced thereby, thus reducing the accumulation of genetic mutations as manifested through aging and carcinogenic processes.

These and other objects of the present invention will become apparent from consideration of the following description of preferred embodiments, examples, claims, and the drawings described below.

Figure 2:
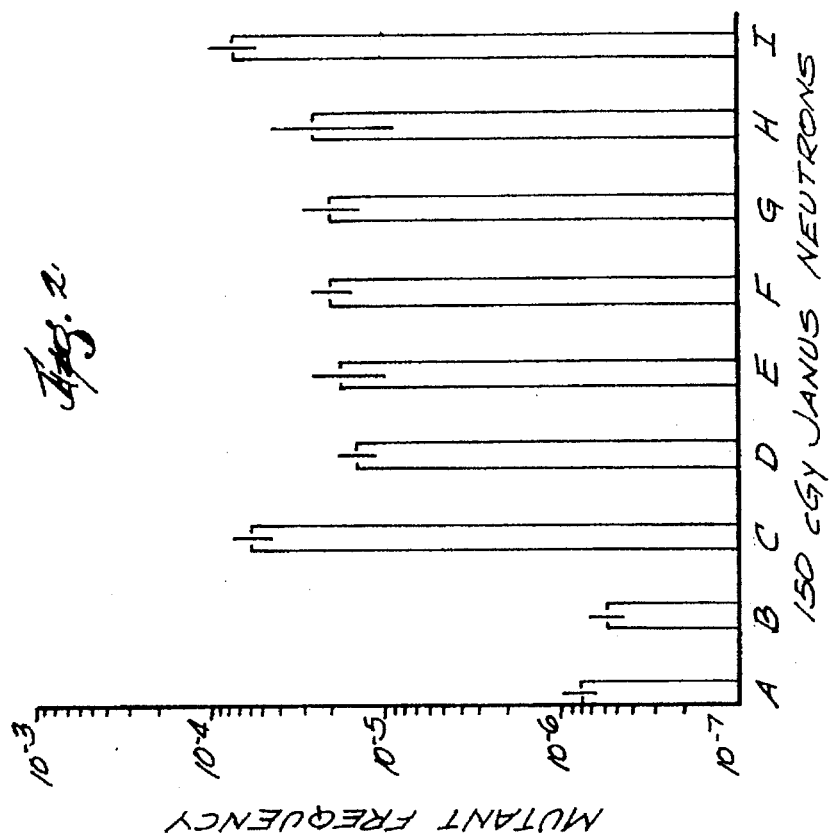
Figure 3:
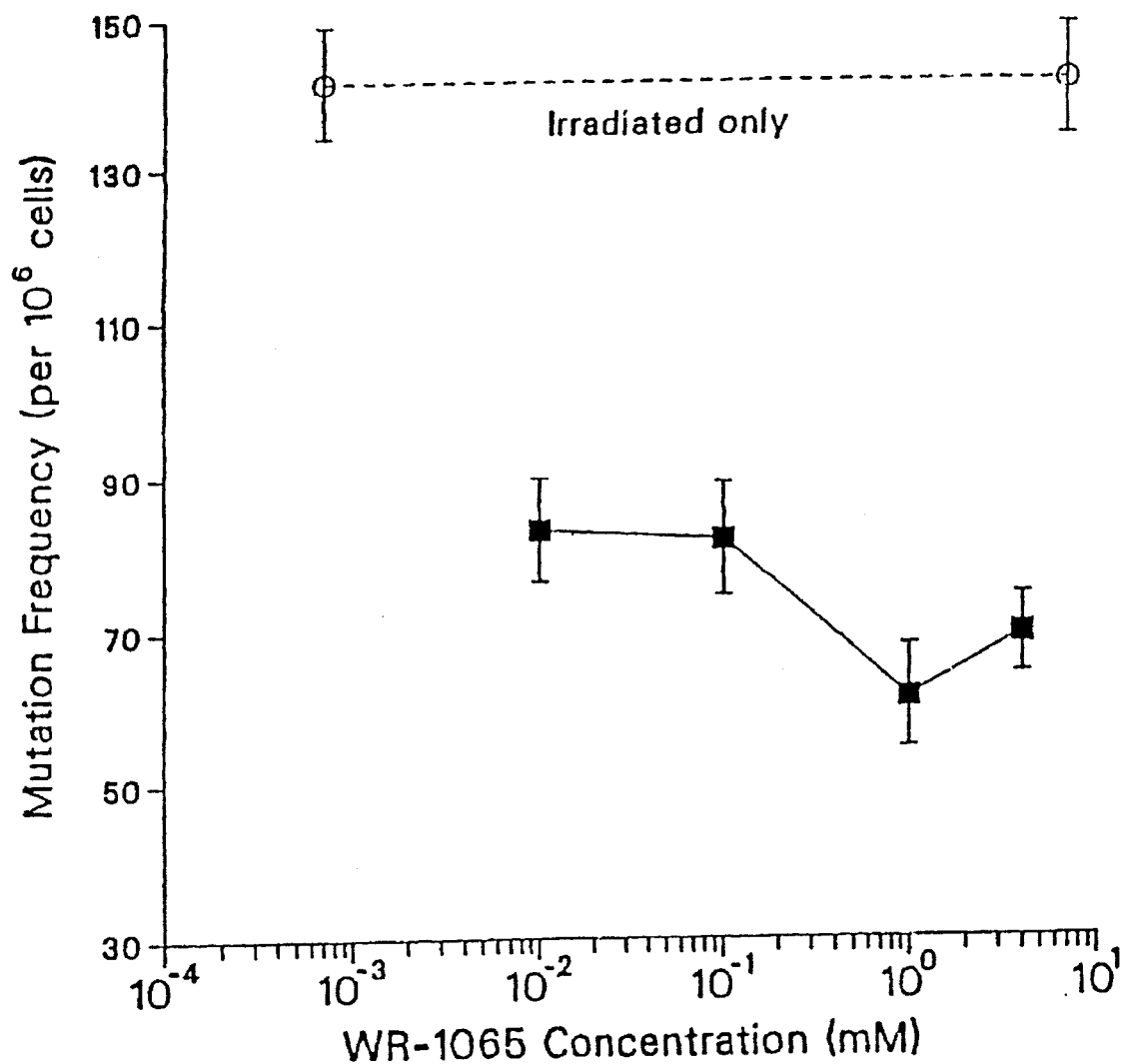
Figure 4:
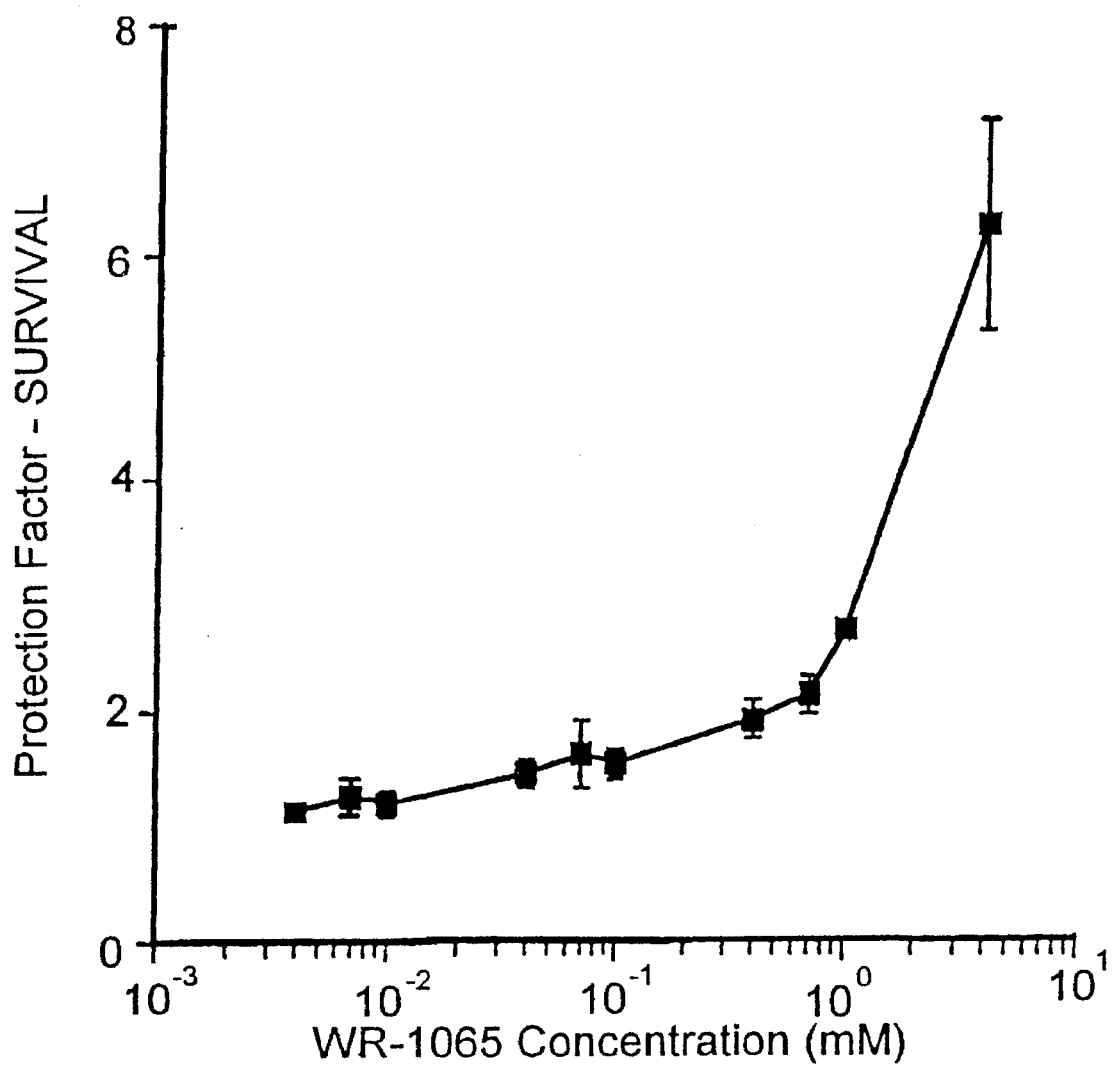
Figure 5A:
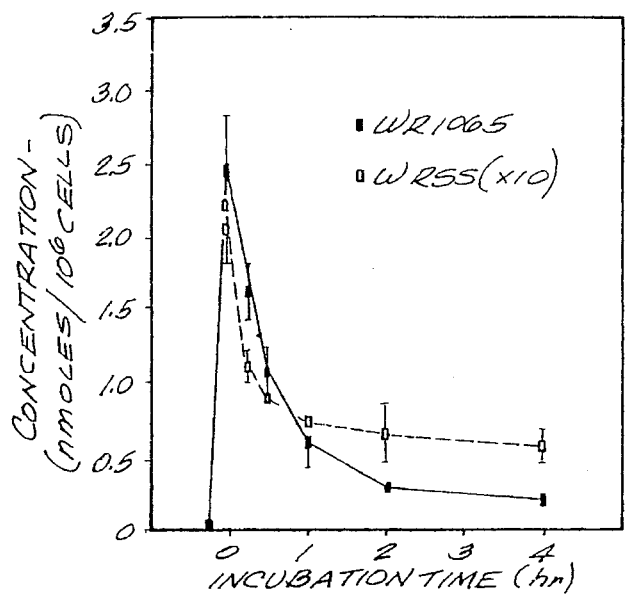
Figure 5B:
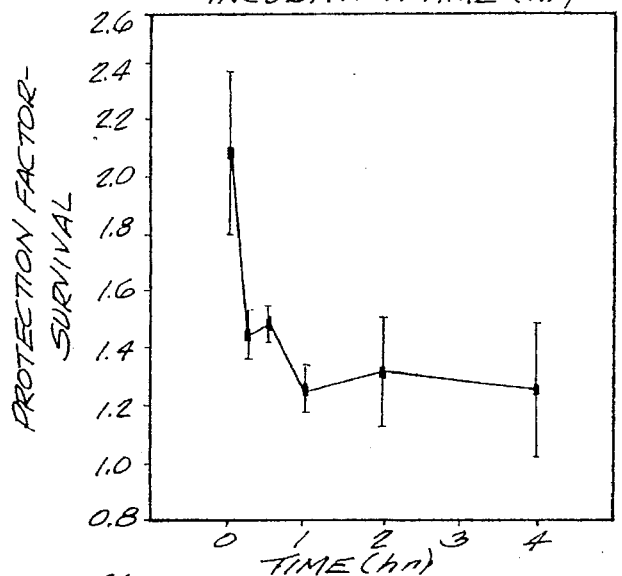
Figure 5C:
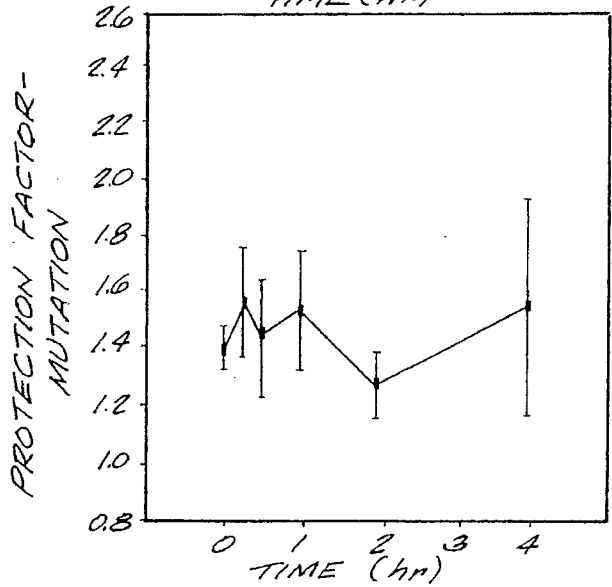
Figure 6:
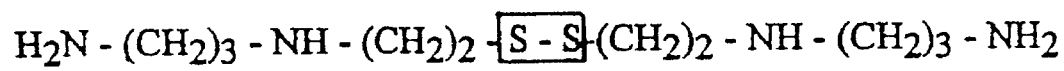
Figure 6:
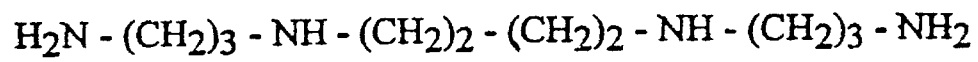
Figure 7B:
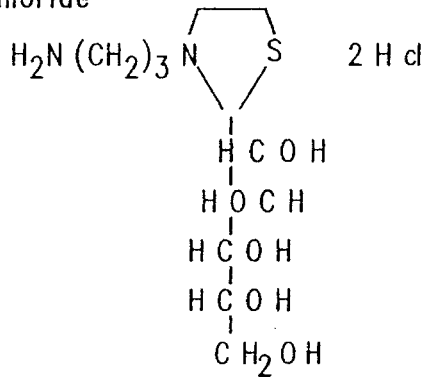
Figure 8:
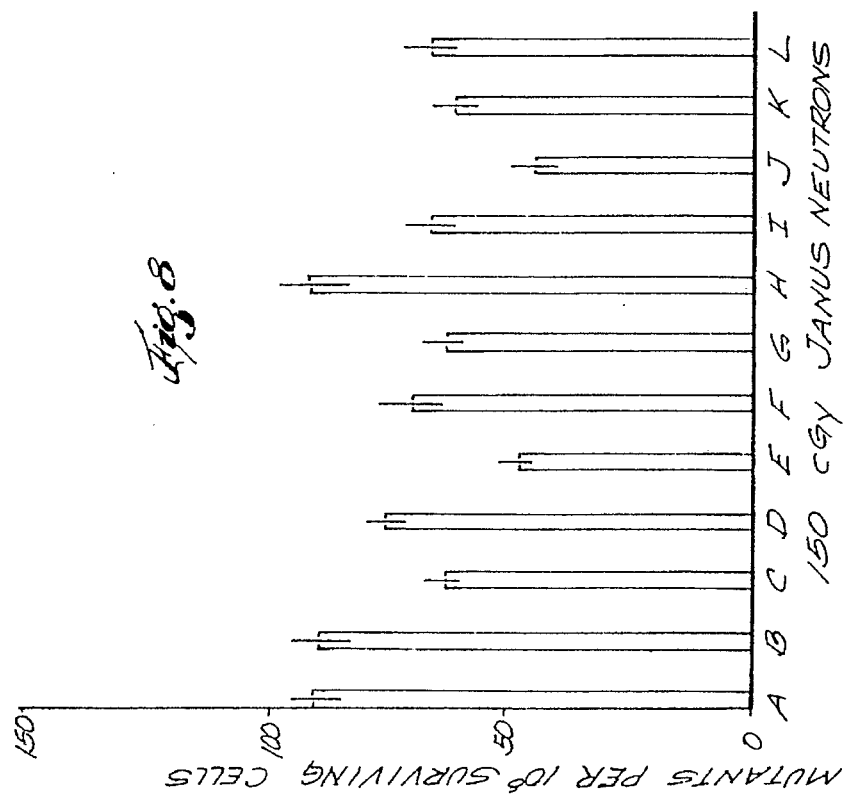

On p.8 in the description of FIG. 2, after the words "10 mg/kg" add A. No treatment; B. WR2721, 400 mg/kg; C. Irradiation only; D. WR2721, 40 mg/kg, before Irradiation; E. WR2721, 200 mg/kg, before Irradiation; F. WR2721, 100 mg/kg, before Irradiation; G. WR2721, 50 mg/kg, before Irradiation; and H. WR2721, 25 mg/kg, before Irradiation; and I. WR2721, 10 mg/kg, before Irradiation. Error bars represent one standard error of the mean;

FIG. 2 demonstrates the performance at low concentrations of S-2-(3-aminopropylamino)ethylphosphorothioic acid (i.e., WR-2721) in the range of from 400 mg/kg to 10 mg/kg. Error bars represent one standard error of the mean;

FIG. 3 demonstrates the relationship between the concentration of 2[(aminopropyl) amino]ethanethiol (i.e., WR-1065) and its protective ability against radiation-induced mutagenesis. Each error bar is one standard error of the mean;

FIG. 4 demonstrates the effect of concentration of 2-[(aminopropyl) amino]ethanethiol (i.e., WR-1065) on its protective ability against radiation-induced lethality. Each error bar is one standard error of the mean;

FIG. 5 demonstrates the effect of cellular levels of 2-[(aminopropyl) amino]ethanethiol (i.e., WR-1065) and its disulfide (i.e., WRSS) on the protection against cell killing in FIG. 5B and protection against mutagenesis in FIG. 5C following irradiation with 150 cGy of fission-spectrum neutrons. Each error bar is one standard error of the mean;

FIG. 6 demonstrates the behavior of the disulfide form (designated WR-33278) of 2-[(aminopropyl) amino] ethanethiol (designated WR-1065) compared to the polyamine spermine;

FIG. 7A and B show the chemical structures of the phosphorothioates/aminothiols used;

FIG. 8 demonstrates the effectiveness under in vitro conditions of 3-[(2-mercaptoethyl)amino]propionamide p-toluenesulfonate (designated WR-2529); S-1-(aminoethyl) phosphorothioic acid (designated WR-638); S-[2-(3-methylaminopropyl amino ethyl]phosphorothioate (designated WR-3689), S-1-(2hydroxy-3-amino)propyl phosphorothioic acid (designated (WR-77913); and 2-[3-methylamino)propylamino]ethanethiol (designated WR-255592) in protecting against radiation-induced mutagenesis. A. Irradiation only; B. WR2529 Before and During; C. WR2529 After; D. WR638 Before and During; E. WR638 After; F. WR3689 Before and During; G. WR3689 After; H. WR77913 Before and During; I. WR77913 after; J. WR55591 Before and During; K. MEA Before and During; and L. MEA After. These results are shown as a function of administration either 30 min before or immediately after irradiation with 150 cGy of fission-spectrum neutrons. Each error bar is one standard error of the mean; and FIG. 9 demonstrates the effectiveness, under in vivo conditions, of S-2-(3-aminopropylamino)ethyl phosphorothioic acid (WR-2721); S-1-(aminoethyl)phosphorothioic acid (WR-638); S-[2-(3-methylaminopropyl)aminoethyl] phosphorothioate acid (WR-3689); S-2-(4-aminobutylamino)ethylphosphorothioic acid (WR-2822); S-2-(5-aminopentylamino)ethyl phosphorothioic aid (WR-2823 ); 1-[3-(3-aminopropyl)thiazolidin-2-Y1]-D-gluco-1,2,3,4,5-pentane-pentol dihydrochloride (WR-255709), in protecting against radiation-induced mutagenesis as a function of administration either 30 min before or immediately after irradiation of B6CF, mice with 150 cGy of fission-spectrum neutrons. A. 750 cGy, $^{60}$Co Gamma-rays; B. WR2721, 400 mg/kg, before Irradiation (pooled); C. WR638 520 mg/kg before; Irradiation; D. WR3689 690 mg/kg before Irradiation; E. WR2822 195 mg/kg before Irradiation; F. WR2823 200 mg/kg before Irradiation; G. WR255709 300 mg/kg, before Irradiation; H. WR2721 400 mg/kg after Irradiation; I. WR2721 400 mg/kg after Irradiation (pooled); J. WR638 520 mg/kg after Irradiation; K. WR2822 195 mg/kg after Irradiation; L. WR2823 200 mg/kg after Irradiation; and M. WR2721 400 mg/kg after Irradiation.

FIGS. 10A–10H demonstrate the inhibitition of topoisomerase IIα activity in CHO K1 cells by the administration of WR-1065, as either thiol- or disulfide-mediated.

FIG. 10A summarizes the effects of WR-1065 and radiation on the activities of Topo I and IIα in K1 CHO cells, as determined by DNA relaxation and unknotting assays, respectively. Comparisons were made to the corresponding untreated control groups using Student's two-tailed t test. Comparisons not significant, $p \geq 0.386$, except as noted.

FIG. 10A summarizes the effects of WR-1065 and radiation on the activities of Topo I and IIα in K1 CHO cells, as determined by DNA relaxation and unknotting assays respectively. Comparisons were made to the corresponding untreated control groups using Student's two-tailed t test. Comparisons not significant $p \geq 0.386$, except as noted.

FIG. 10B summarizes the effects of WR-1065 and radiation on the protein levels of Topo IIα in K1 CHO cells, as determined by immunoblotting using an anti-Topo II specific antibody. Comparisons were made to the corresponding untreated control groups using Student's two-tailed t test. All comparisons not significant, $p > 0.300$.

Figure 10C:
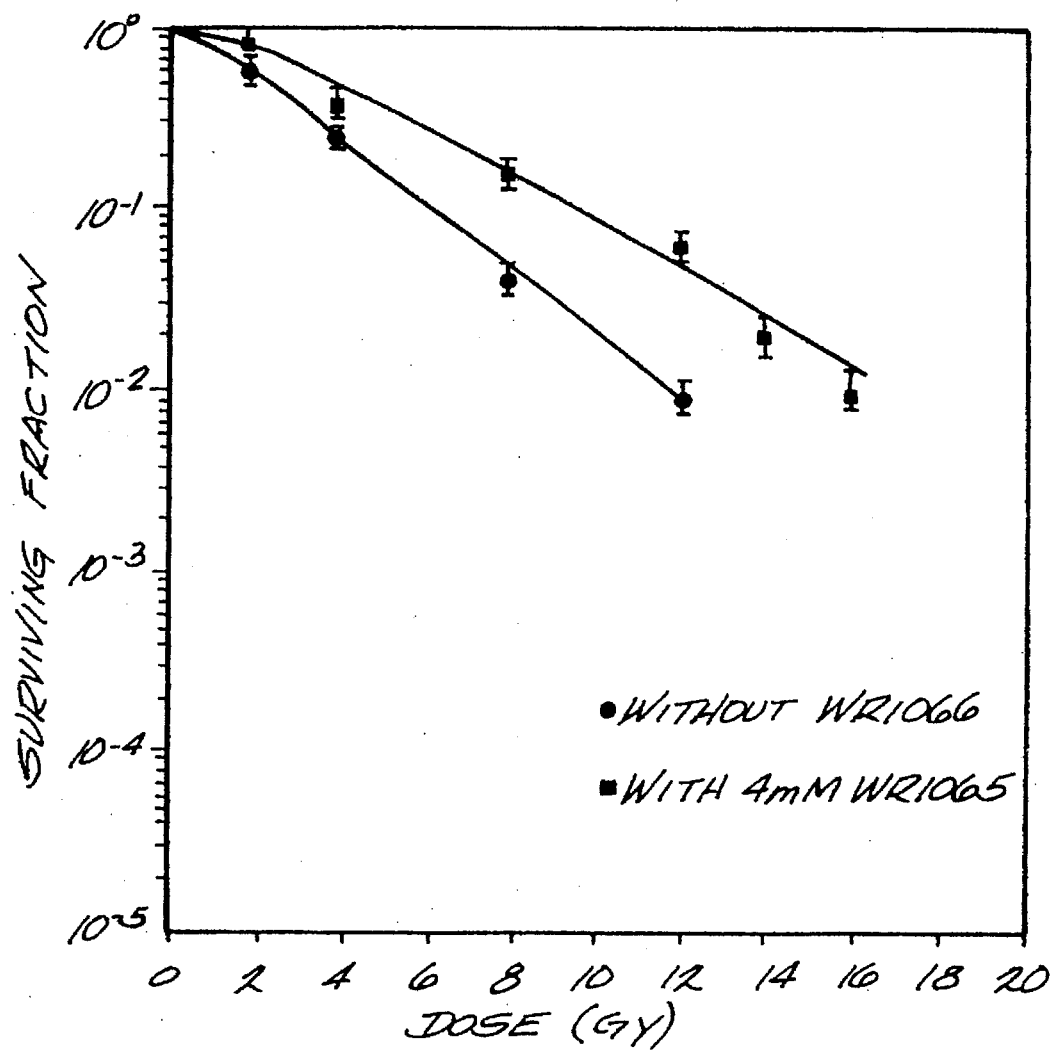

FIG. 10C shows survival curves for K1 cells irradiated with 50-kVp x-rays. Cells were either treated with 4 mM WR-1065 (■) or untreated (●). Experimental points represent the mean of three experiments; error bars represent the standard error of the mean. Survival curve parameters were determined by using a computer-fitted least-squares regression model.

FIGS. 10Di and ii show, respectively, Topo IIα and topo I activity in nuclear extracts from untreated and WR-1065-treated K1 cells. Nuclear extracts containing the following amounts of protein were assayed for topo IIα-mediated unknotting and topo-I-mediated relaxing activities, as described in Materials and Methods: FIG. 10Di, lane 1, 80 ng; lane 2, 40 ng; lane 3, 20 ng; lane 4, 10 ng; lane 5, 5 ng; FIG. 10Dii, lane 1, 100 ng; lane 2, 30 ng; lane 3, 10 rig; lane 4, 3 ng; lane 5, 1 ng; (–), no nuclear extract. This is a representative experiment. Data from four such experiments Were used to determine the mean activities.

Figure 10E:
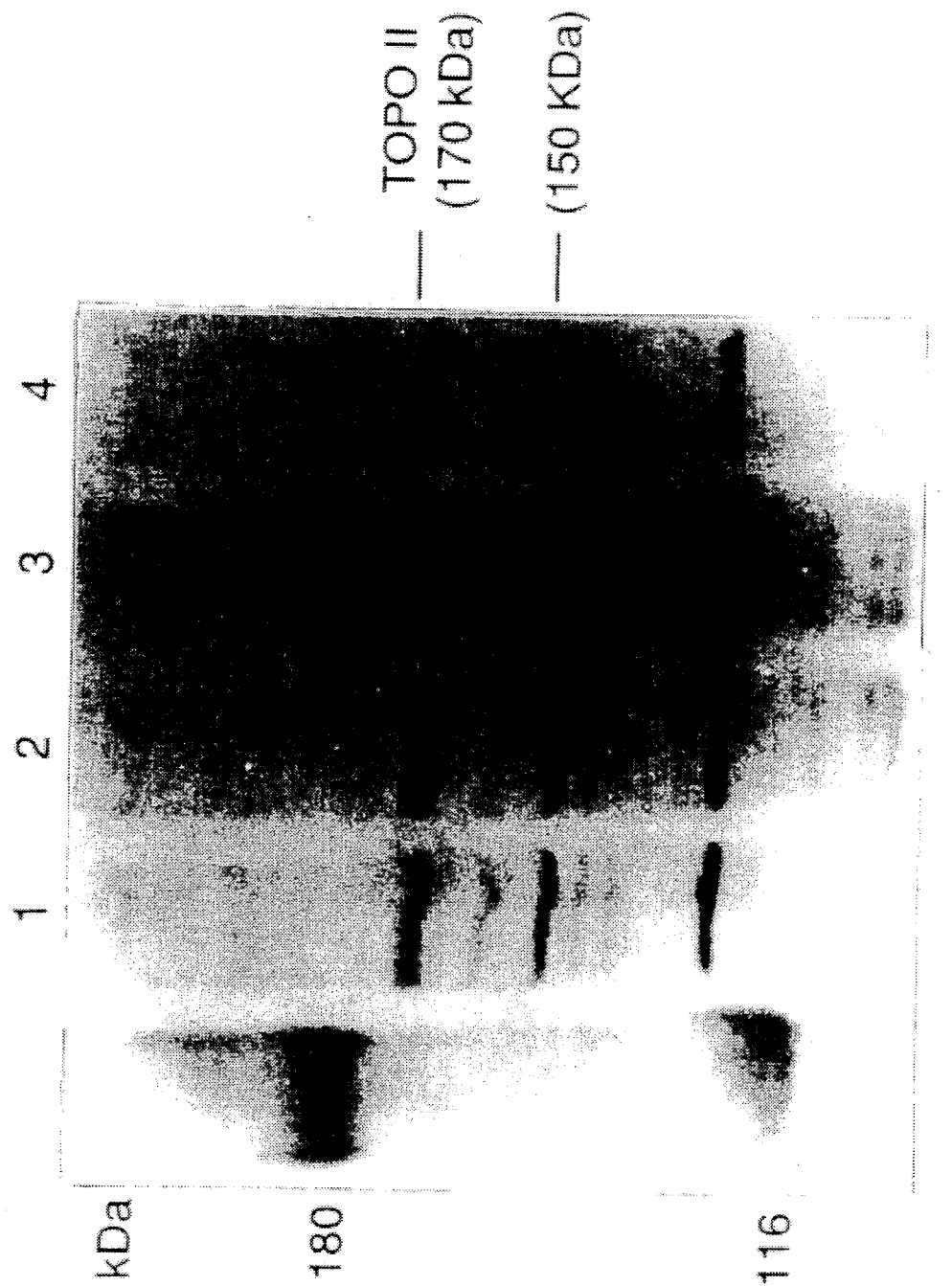

FIG. 10E results from immunoblot analysis of topo IIα levels in nuclear extracts from untreated and WR-1065-treated K1 cells. Logarithmically growing cells were washed twice by centrifugation at 1000×g for 5 min in PBS containing protease inhibitors and extracts. Nuclear proteins were subjected to gel electrophoresis through an 8% SDS-polyacrylamide gel and transferred to nitrocellulose. Blots were incubated with anti-topo II antibody. The molecular weights shown on the right ordinate are those of topo IIα (MW 170,000) and its proteolytic products. Prestained standards with their molecular weights in thousands are shown on the left ordinate. Lane 1, untreated cells; lane 2, WR-1065-treated but unirradiated cells, lane 3; irradiated cells; lane 4, cells irradiated and treated with WR-1065.

Figure 10F:
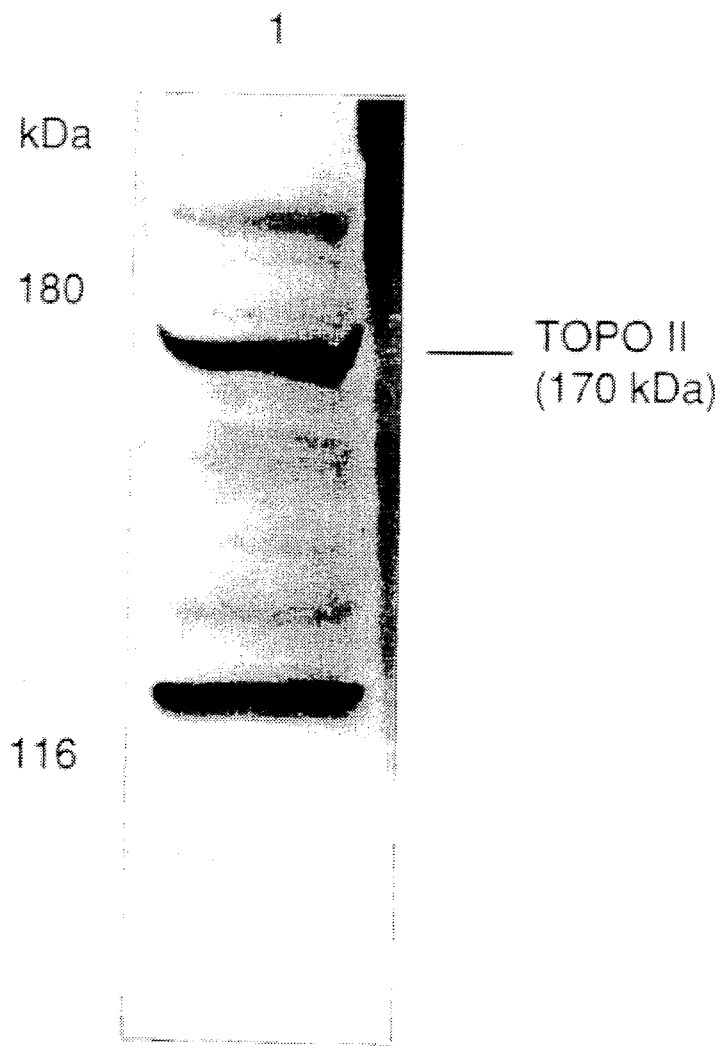

FIG. 10F results from immunoblot analysis of topo IIα levels in rapidly lysed cells. Conditions were similar to those described in FIG. 10E with the exception that cells were lysed in electrophoresis sample buffer containing 2% SDS by boiling for 2 min.

Figure 10G:

FIGS. 10Gi and ii show, respectively, topo I (FIG. 10Gi) and topo IIα (FIG. 10Gii) activity in cell-flee extracts. Reaction mixtures were assayed for topo I-mediated relaxation of pUC8 plasmid DNA and topo IIα-mediated unknotting of P4 phage DNA, as described in Materials and Methods: FIG. 10Gi, lane 1, pUC8 DNA only; lane 2, no drug; lane 3, 0.4 mM WR-1065, lange 4, 4 mM WR-1065; lane 5, 40 mM WR-1065; lane 6, 0.5 mM Camptothecin. FIG. 10Gii, lane 1, no drug; lane 2, 0.4 mM WR-1065; lane 3, 4 mM WR-1065; lane 4, 40 mM WR-1065; lane 5, 0.3 mM Genistein.

Figure 10H:
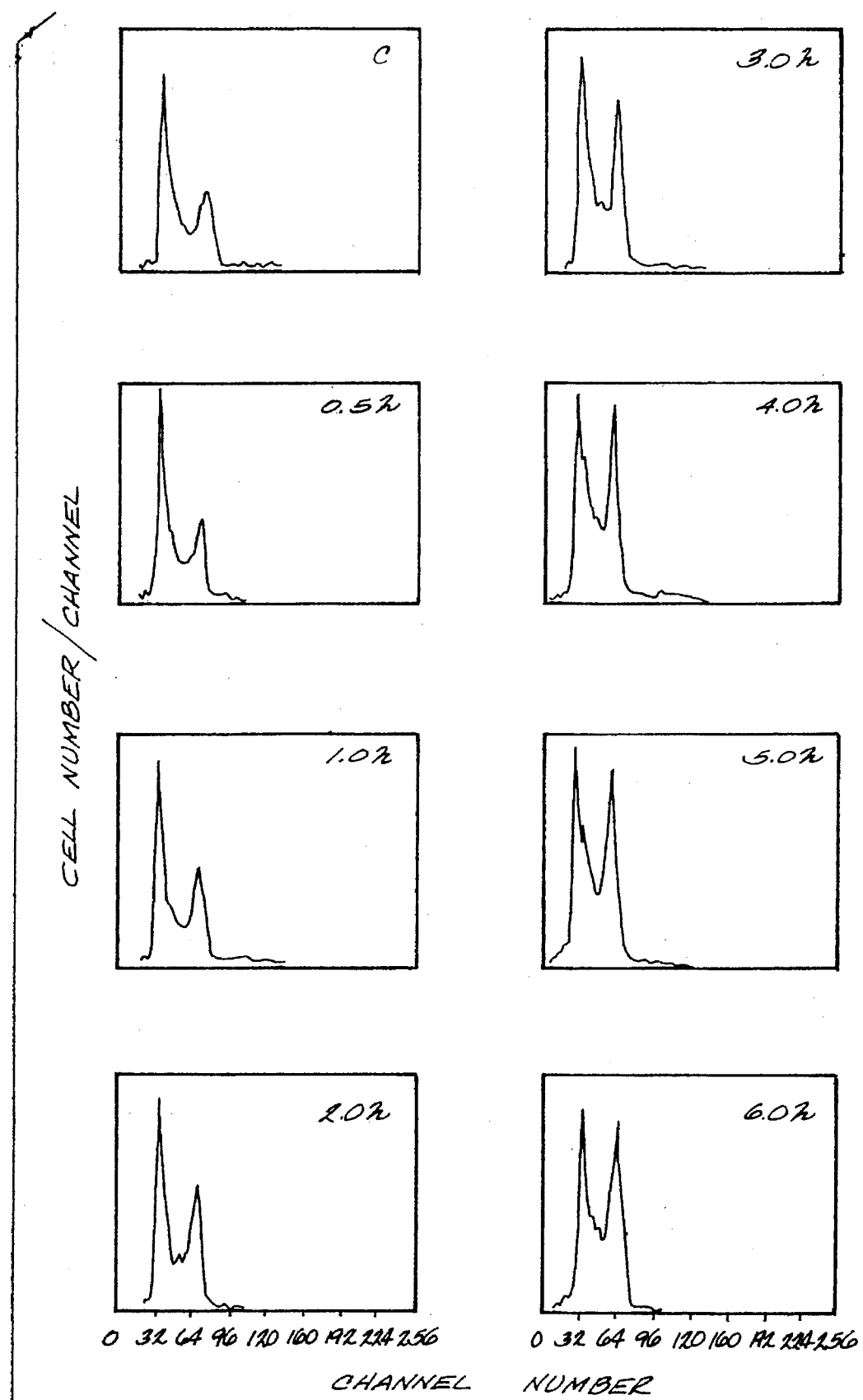

FIG. 10H shows typical flow cytometry patterns describing the DNA distribution of K1 cells exposed to 4 mM WR-1065 for 0 rain, 30 min, 1–6h. During the 6 h exposure, the percent of cells in G1 fell from 39 to 21, while the percent of cells in G2 increased from 18 to 27. The percent of cells in S ranged from 43 to 460.

FIGS. 11A–11D demonstrate the identity in mutations observed in both mouse and human T-lymphocytes at the HPRT locus, upon treatment with cytoxan—as is also observed after irradiation. The anti-mitagenic effect of WR-2721 and/or its associated metabolites was demonstrated in mice treated with cytoxan or cisplatin. Each error bar is one standard error of the mean.

FIGS. 12A–12K illustrate the anti-mutagenic effect of WR-33278 electroporated into CHO AA8 cells.

FIGS. 12A and 12B. Effects of WR-33278 (▫) and spermine (▮) on CHO AA8 cell survival (FIG. 12A) and mutation induction at the hprt locus (FIG. 12B). Drug-only bars represent the effects of 0.01 mM WR-33278 or 0.01 mM spennine on these processes. FIG. 12A: compared with its corresponding drug exposure only group, all cell survivals in each of the electroporated groups are significantly reduced (student's two-tailed t test, $P \geq 0.001$). FIG. 12B: compared with its corresponding drug exposure only group, the number of mutants per $10^6$ surviving cells in each of the electroporated groups is not significantly different ($P \geq 0.01$). Data presented are from a minimum of 3 replicate experiments. Error bars represent one standard error of the mean.

FIGS. 12C and 12D. Effect of electroporation on radiation-induced cell killing (FIG. 12C) and mutagenesis at the hprt locus (FIG. 12D). FIG. 12C: as compared with cell killing by radiation only, cell survival was significantly reduced by electroporation performed 30 min before (P=0.007) or 3 h after (P≧0.001) irradiation. FIG. 12D: mutation induction was significantly enhanced by electroporation performed 30 min before (P≧0.001) or 3 h after (P≧0.001) irradiation. Experiments were repeated a minimum of 3 times. Error bars represent one standard error of the mean.

Figure 12F:
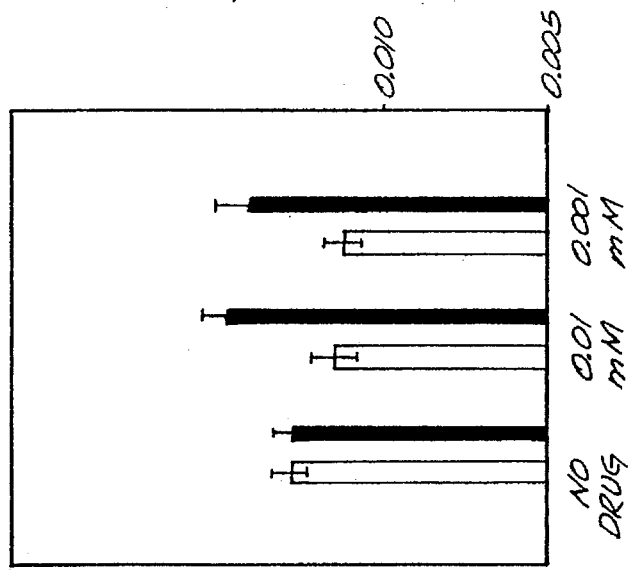
Figure 12E:
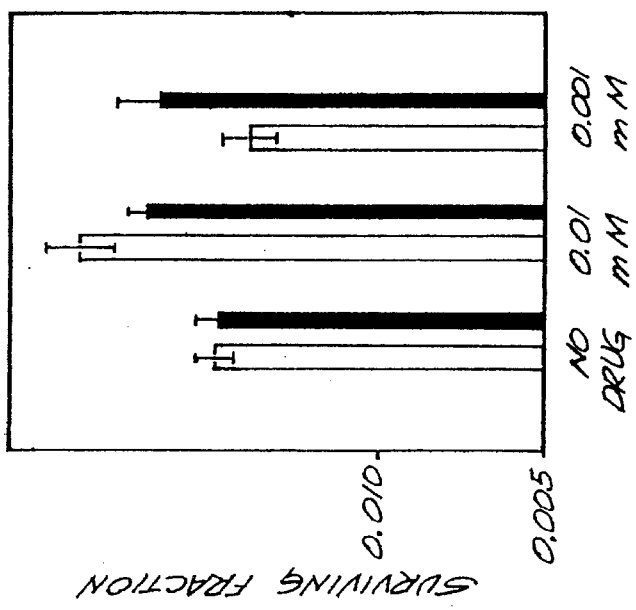

FIGS. 12E and 12F. Effect of electroporation with either WR-33278 (□) or spermine (■) on the survival of cells irradiated with 750 cGy either 30 min after (FIG. 12E) or 3 h before (FIG. 12F) electroporation. FIG. 12E: comparing electroporation with no drug 30 min prior to irradiation, electroporation of 0.01 mM WR-33278 or spermine 30 min prior to irradiation significantly protected against cell killing (P=0.006 and P=0.0 13, respectively). FIG. 12F: comparing electroporation with no drug 3 h after irradiation, electroporation of WR-33278 did not affect cell survival (0.01 mM, P=0.1; and 0.001 mM, P=0.1). Electroporation of spermine at a concentration of 0.01 mM was more effective (P=0.01) than a concentration of 0.001 mM (P=0.33). All experiments were repeated a minimum of 3 times. Error bars equal one standard error of the mean.

Figure 12H:
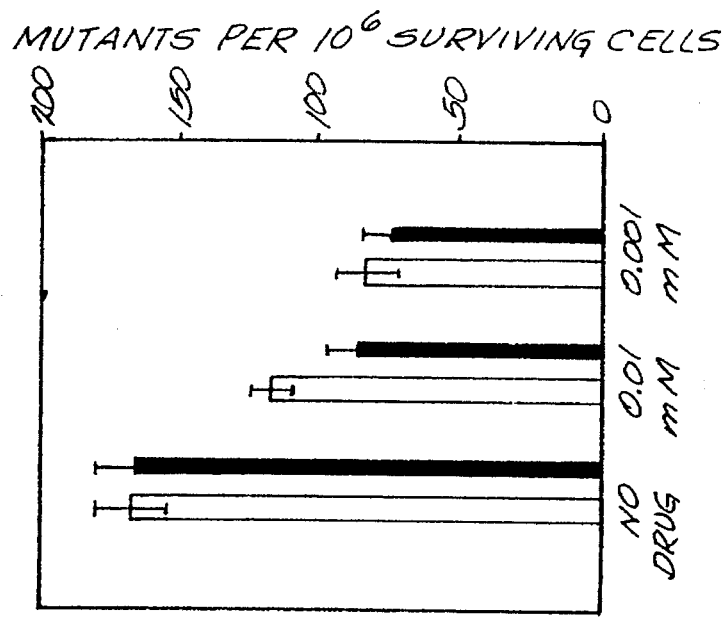
Figure 12G:
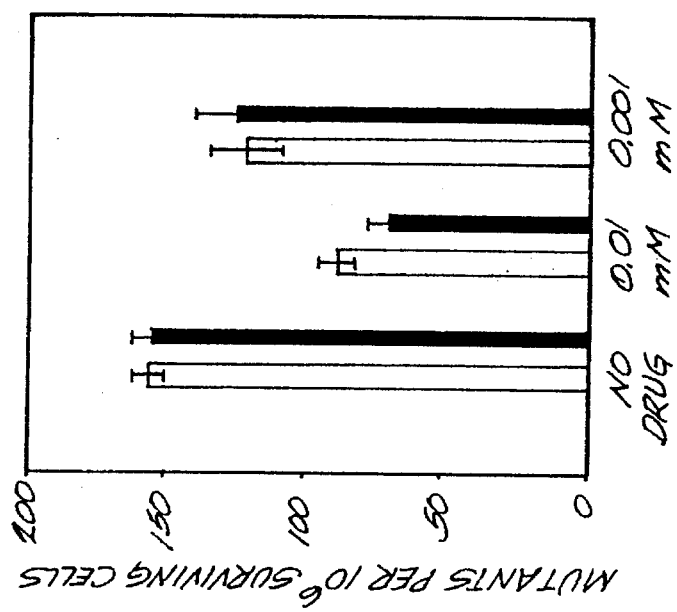

FIGS. 12G and 12H. Effect of electroporation with either WR-33278 (□) or spermine (■) on hprt mutation induction in cells irradiated with 750 cGy either 30 min after (FIG. 12G) or 3 h before (FIG. 12H) electroporation. FIG. 12G: comparing electroporation with no drug 30 min prior to irradiation, electroporation of both 0.01 mM and 0.001 mM WR-33278 or spermine were highly effective in protecting against the induction of hprt mutants (P>0.001, P=0.015, P>0.001, P=0.04, respectively). FIG. 12H: comparing electroporation with no drug 3 h following radiation, electroporation of both 0.01 mM and 0.001 mM WR-33278 or spermine were highly effective in protecting against the induction of hprt mutants (all P values>0.001). All experiments were repeated a minimum of 3 times. Error bars represent one standard error of the mean.

Figure 12I:
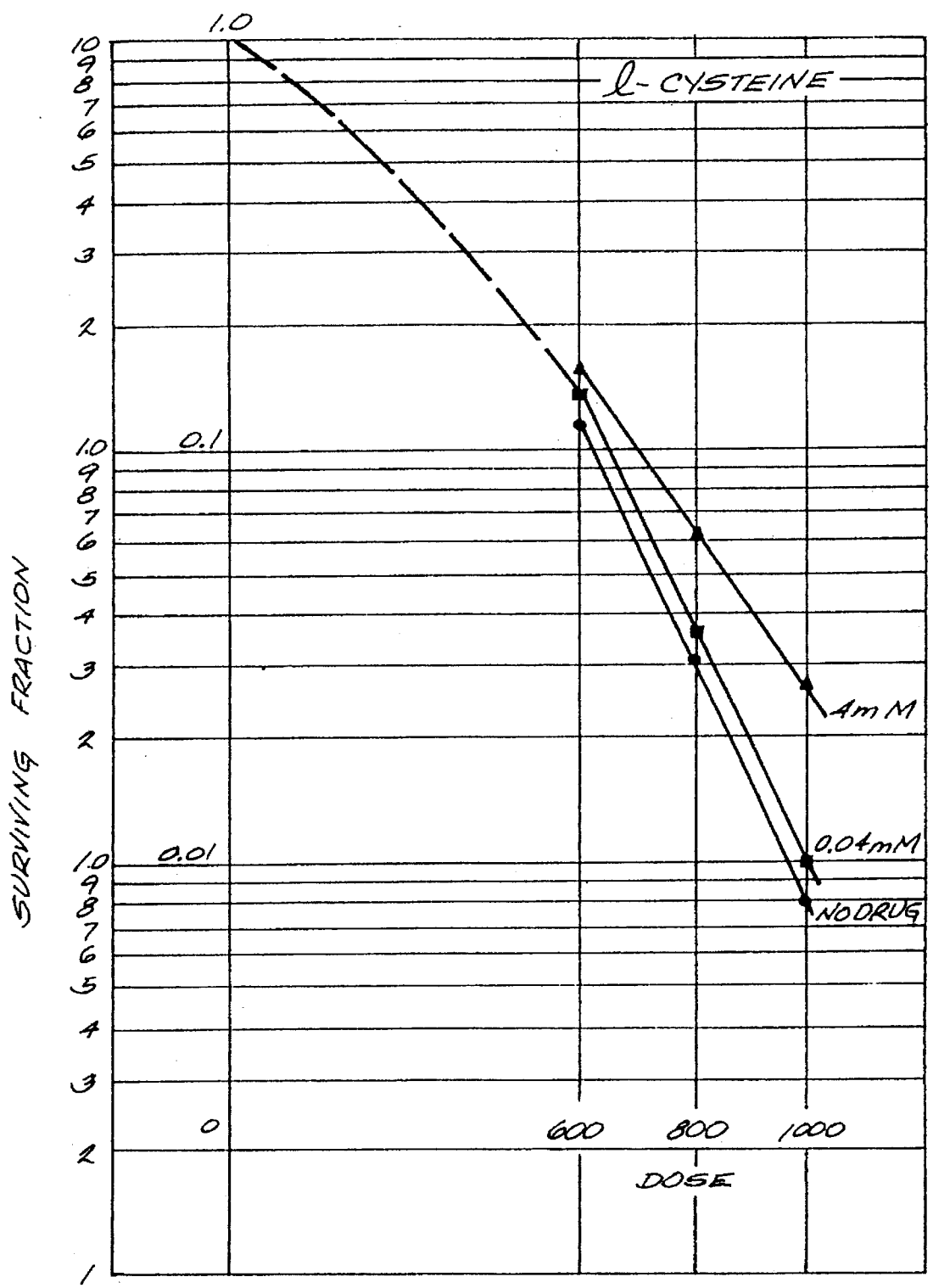
Figure 12J:
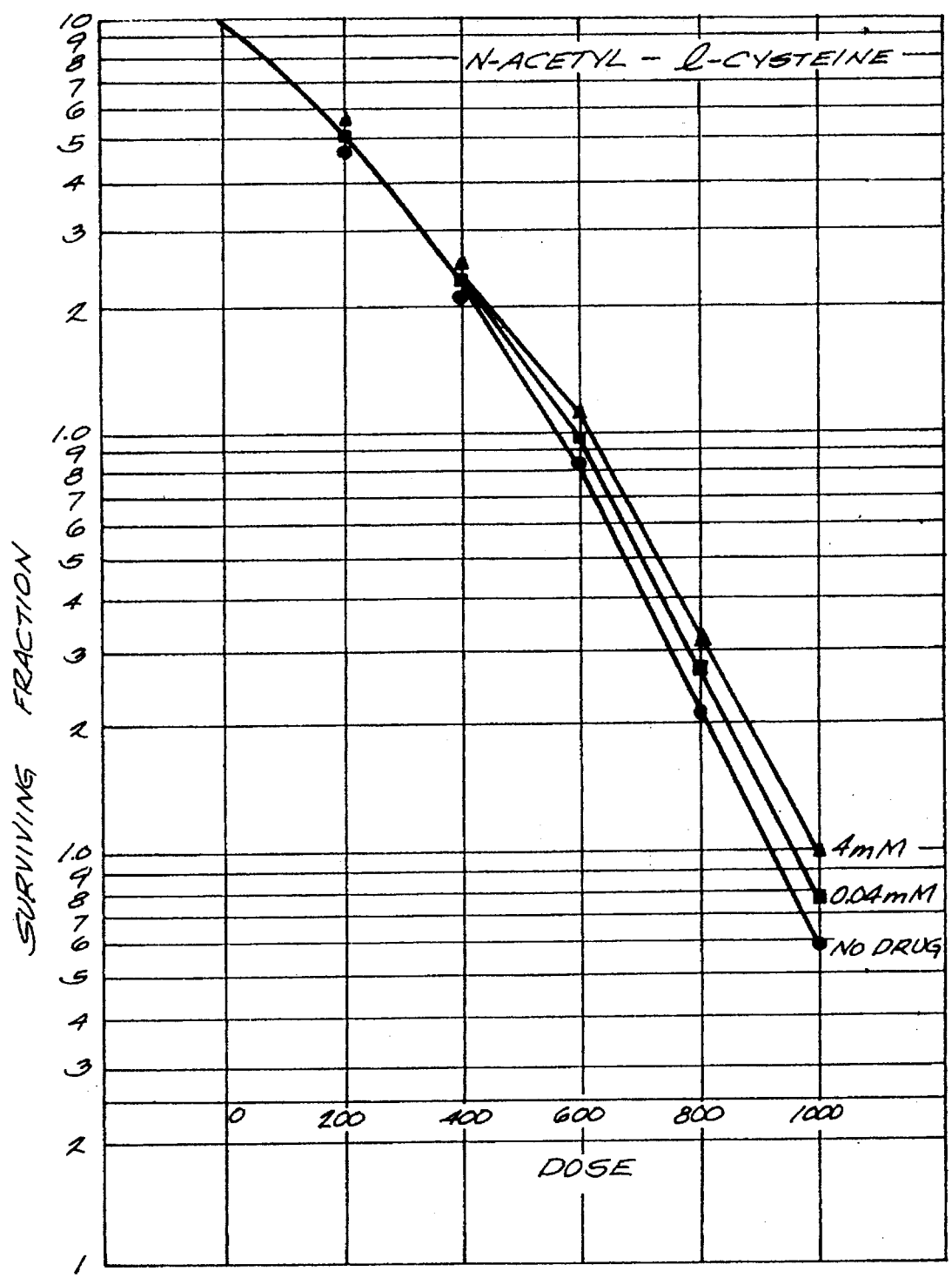
Figure 12K:
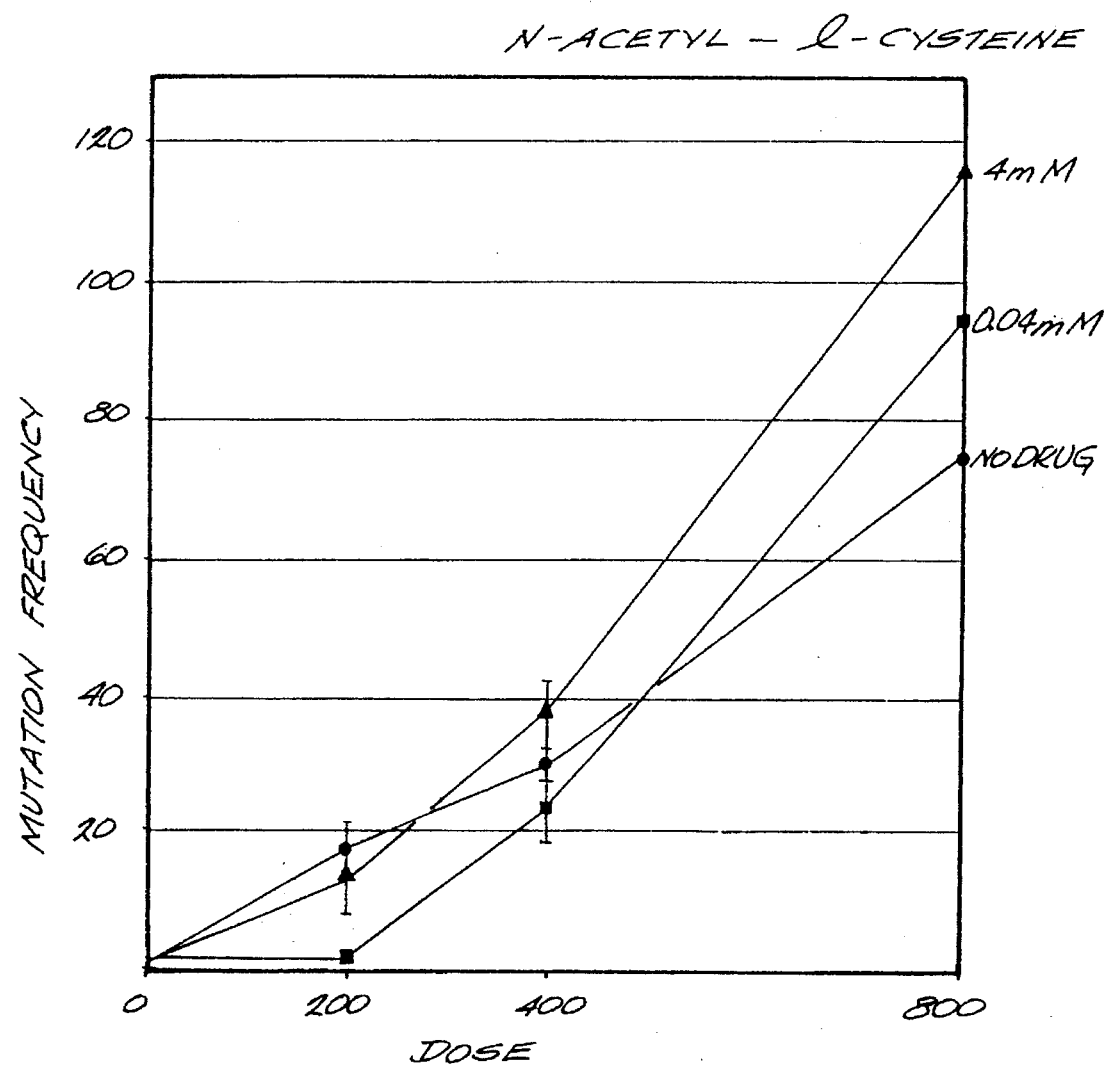

FIGS. 12I–12K illustrate the role performed by the presence of an amine functionality, as evidenced through a comparison of 1-cysteine and N-acetylcysteine. Each error bar is one standard error of the mean.

DESCRIPTION OF THE PREFERRED EMBODIMENTS

The present invention is concerned with four general areas: (1) phosphorothioates and associated metabolites, when administered to mammals (i.e., mice) following mutagen exposure (i.e., ionizing radiation including photon and fission-spectrum neutrons and chemical mutagens such as cis-diaminedichloroplatinum (II) (cisplatin) and cytoxan), protect against genotoxic damage which normally leads to the development of somatic mutations—the same mutations observed in human lymphocytes; (2) protection against mutagen-induced mutations by the phosphorothioates and associated metabolites at very low concentrations which are much less than required for protection against cell lethality; (3) protection against mutagen-induced somatic mutations by the phosphorothioates and associated metabolites, as shown to correlate most closely with the disulfide metabolite and the presence of a polyamine functionality; and (4) protection against mutagen-induced somatic mutations, as a general property of the genus of phosphorothioates and their associated metabolites irrespective of the origin of the mutagenic event; all of which are demonstrated by the observed antimutagenic properties of the species S-1-(aminoethyl) phosphorothioic acid (WR-638), S-[2-(3-methylaminopropyl)aminoethyl] phosphorothioate (WR-3689), S-2-(4-aminobutylamino)ethylphosphorothioic acid (WR-2822), 3-[(2-mercaptoethyl)amino]propionamide p-toluenesulfonate (WR-2529), S-1-(2-hydroxy-3-amino)propyl phosphorothioic acid (WR-77913), 2-[3-(methylamino)propylamino]ethanethiol WR-255591), S-2-(5-aminopentylamino)ethyl phosphorothioic acid (WR-2823), and 1-[3-(3-aminopropyl)thiazolidin-2-yl]-D-gluco- 1,2,3,4,5 pentanepentol dihydrochloride (WR-255709).

I. Phosphorothioate Genus Protection After Irradiation.

Figure 1:
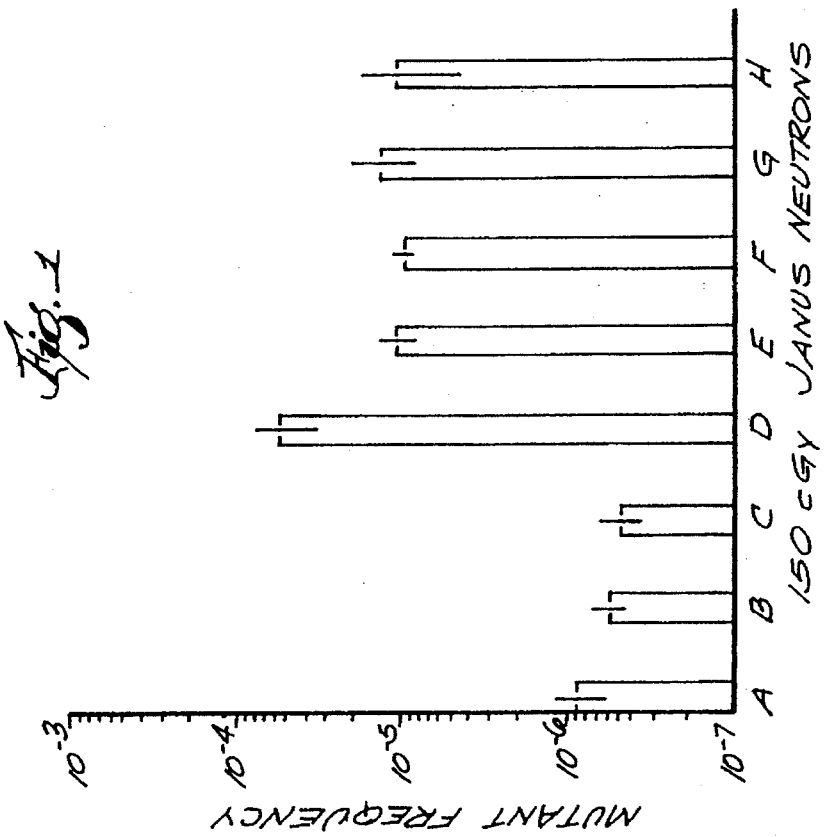
FIG. 1 demonstrates the performance of S-2-(3-aminopropylamino)ethylphosphorothioic acid (also identified as WR-2721) to protect against radiation-induced mutagenesis when administered to animals either 30 min before, immediately after, or 3 h following irradiation. A. No treatment; B. WR2721, 400 mg/kg; C. WR2721, 400 mg/kg (3 times) D. Irradiation only; E. WR2721 before Irradiation; F. WR2721 after Irradiation; G. WR2721 3 hr after Irradiation; and H. WR2721 3,24,48 hr after Irradiation.

Chemicals of the phosphorothioate genus and associated metabolites can protect against somatic mutations when administered to mammals following a mutagen exposure. This conclusion is based on the observation that S-2-(3-aminopropylamino)ethyl phosphorothioic acid, administered at a dose of 400 mg/kg up to 3 h following neutron radiation exposure, affords substantial protection against radiation-induced mutations at the hypoxanthine-guanine phosphoribosyl transferase locus in the T lymphocytes of mice (see FIG. 1, ref. 10). The magnitude of protection is unchanged regardless of whether the phosphorothioate was administered 30 min before, immediately following (i.e., within 10 min), or up to 3 h following irradiation of the test animals.

The spontaneous mutant frequency of T lymphocytes from unirradiated control animals was stable and ranged from $9$–$10 \times 10^{-7}$. Following irradiation with 150 cGy of fission neutrons, the mutant frequency increased to $5.6 \times 10^{-5} \pm 2.3 \times 10^{-5}$ (1 standard error of the mean). Mutant frequencies in animals administered S-2-(3-aminopropylamino)ethylphosphorothioic acid 30 min before immediately after, or 3 h following irradiation with 150 cGy of fission neutrons were $1.1 \times 10^{-5} \pm 2.6 \times 10^{-6}$, $1.0 \times 10^{-5} \pm 1.3 \times 10^{-6}$, and $1.4 \times 10^{-5} \pm 5.8 \times 10^{-6}$, respectively.

As stated above, the aminothiol 2-[(aminopropyl)amino] ethanethiol (WR-1065) is the active thiol of S-2-(3-aminopropylamino)ethylphosphorotioic acid (WR-2721). Aminothiols, such as WR-1065 and its associated disulfide metabolite, are effective in inhibiting DNA synthesis, strand rejoining, nuclease activity, and cell cycle progression in mammalian cells. These effects on cellular enzymatic processes indicate aminothiol protection against mutagenesis includes modulation of endogenous enzyme processes relating to DNA synthesis and repair. WR-1065 is an effective radiation protector and antimutagenic agent when it is administered 30 min prior to radiation exposure to Chinese hamster ovary K1 cells (i.e., a dose modification factor of 1.4) at a concentration of 4 mM. Under these exposure conditions, topoisomerase (topo) I and IIα activities and associated protein contents were measured in the K1 cell line using the DNA relaxation assay, the P4 unknotting assay, and immunoblotting, respectively. WR-1065 was ineffective in modifying topo I activity, but it did reduce topo IIα activity by an average of 50 percent. The magnitude of topo IIα protein content, however, was not affected by these exposure conditions. (See FIGS. 10A–G.) Cell cycle effects were monitored by the method of flow cytometry. Exposure of cells to 4 mM WR-1065 for a period of up to 6 h resulted in a buildup of cells in the G2 compartment. (FIG. 10H.) This observed cell cycle delay in conjunction with reduction in topo IIα activity indicates more time available for the repair of cell damage and suggests genome stabilization and increased efficiency of repair processes.

These results demonstrate, in particular, a modifying effect by 2-[(aminopropyl)-amino]ethanethiol on type II topoisomerase, which is involved in DNA synthesis. In contrast to typical topo II inhibitors used in chemotherapy, WR-1065 and/or its disulfide are effective agents against both radiation-induced cell lethality and mutagenesis. At concentrations up to 40 mM, WR-1065 did not affect the activity of either topo II or topo IIα, as compared to inhibitors Camptothecin and Genistein, suggesting, without being bound to any one theory or mechanism of operation, that WR-1065-induced reduction in topo IIα activity may be due to some indirect effect. Without limitation, this observation may involve inhibition of protein kinase C-mediated metabolic phosphorylation of topo IIα by WR-1065. Inhibiting phosphorylation could reduce the activity of enzymes that serve as substrates for this protein kinase. This possible mode of action is consistent with the observed reduction in the catalytic activity of topo IIα and WR-1065-treated K1 cells (determined by the unknotting assay), without a concomitant reduction of topo IIα protein levels (determined by immunoblotting).

The topoisomerase studies demonstrate the ability of phosphorothioates and associated metabolites to influence cellular response to mutagenic insult and cellular enzymatic activities involved in DNA synthesis, cell cycle progression and, possibly, repair.

Figure 11B:
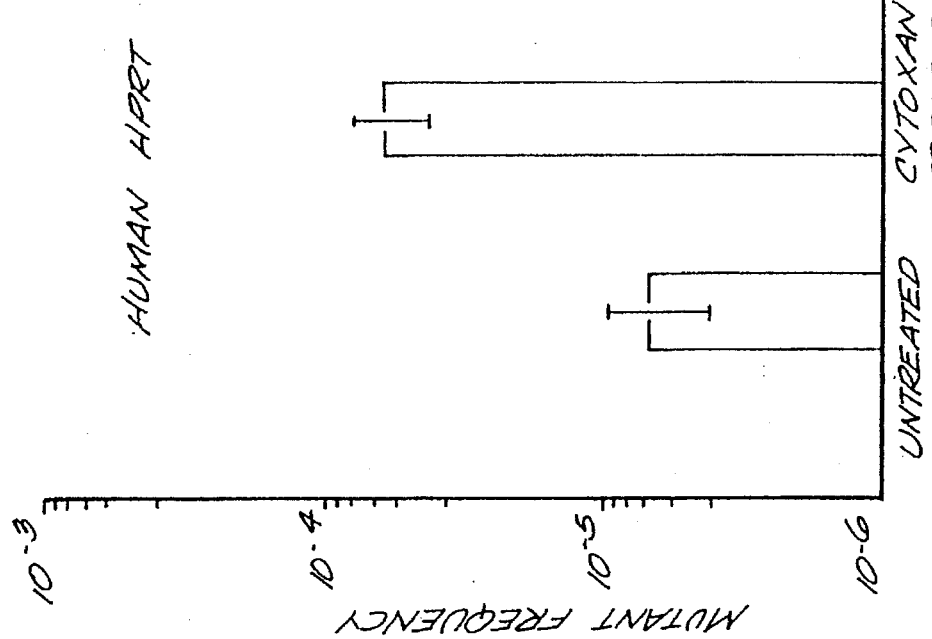
Figure 11A:
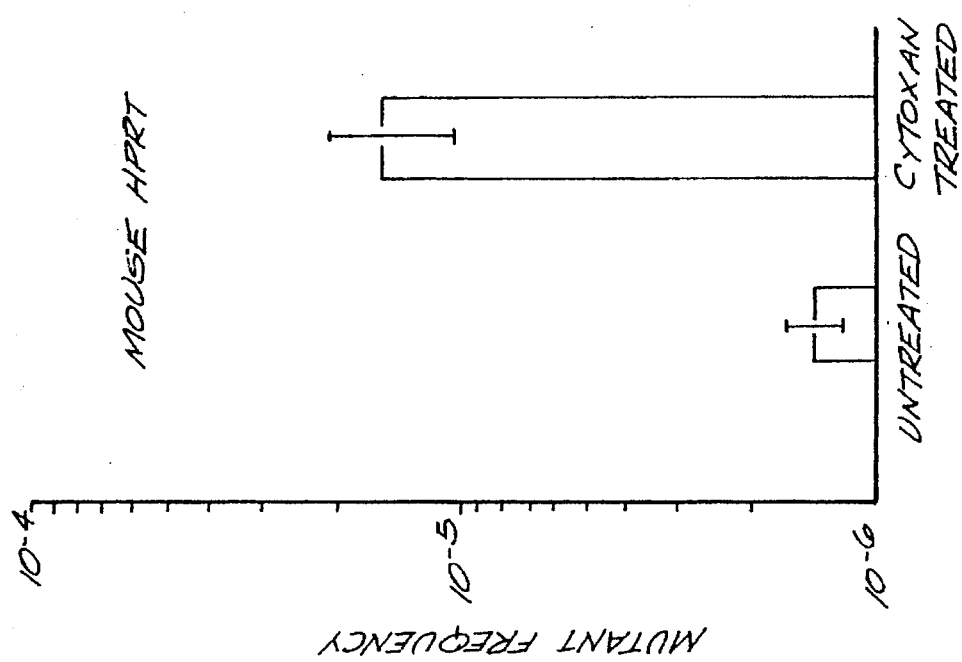

Referring to FIGS. 11A and 11B, mice and human cancer patients, respectively, were treated with cytoxan and observed with respect to the increase in mutant frequency. As shown, in comparison with untreated populations, both the mouse and human subjects exhibited substantial cytoxan-induced mutations at the hypoxanthine-guanine phosphoribosyl transferase (hprt) locus-consistent with the radiation-induced mutagenesis, described above, and supporting the proposition that the same mutation is observed irrespective of the nature and/or source of the mutagenic event. The mutant frequencies of mice T-lymphocytes were determined as described above. The human lymphocytes were obtained from blood samples of patients after the cytoxan treatment, using standard cell stimulation techniques and hprt assays.

Figures 11C, 11D:
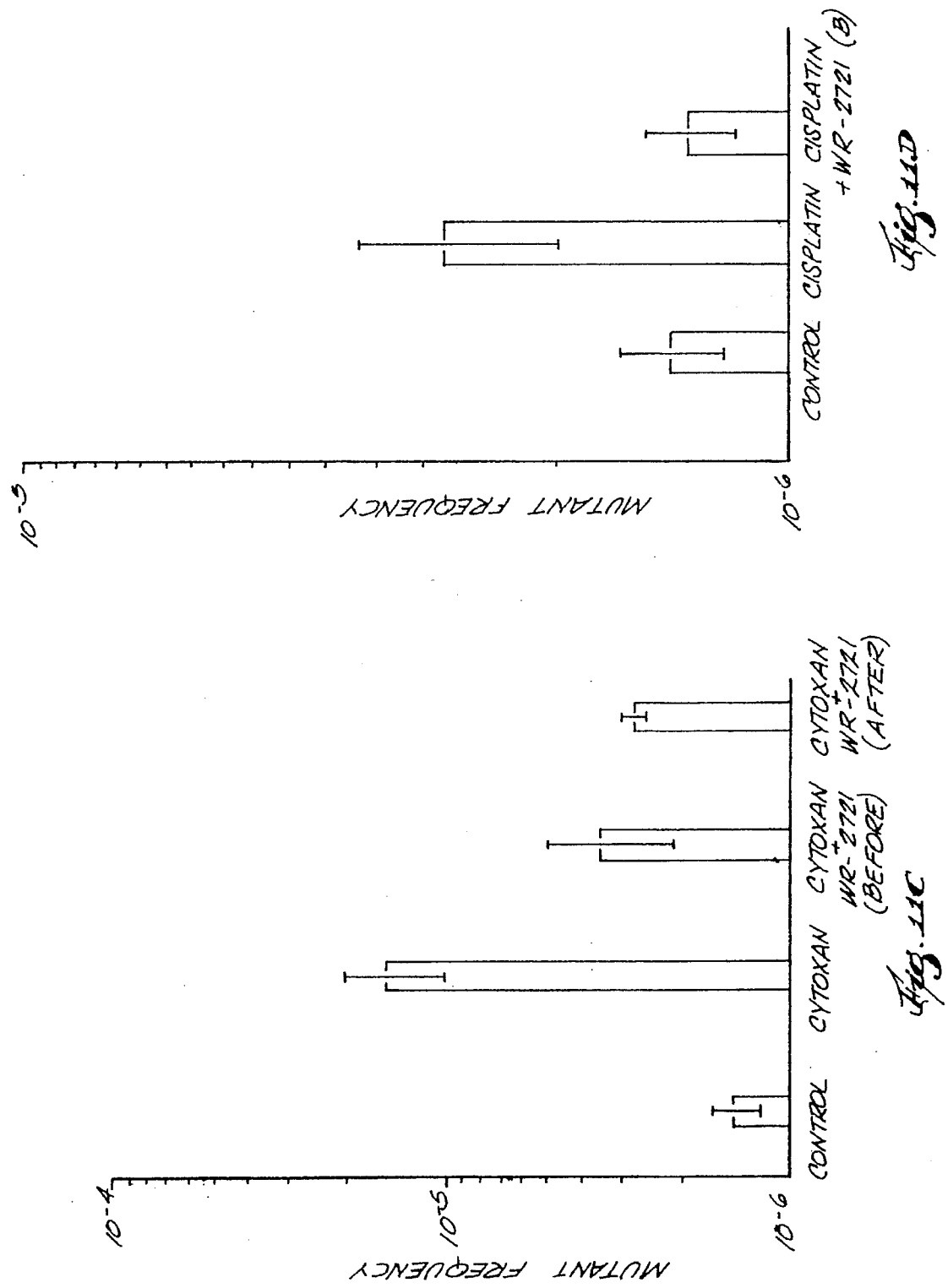
Figure 11B:
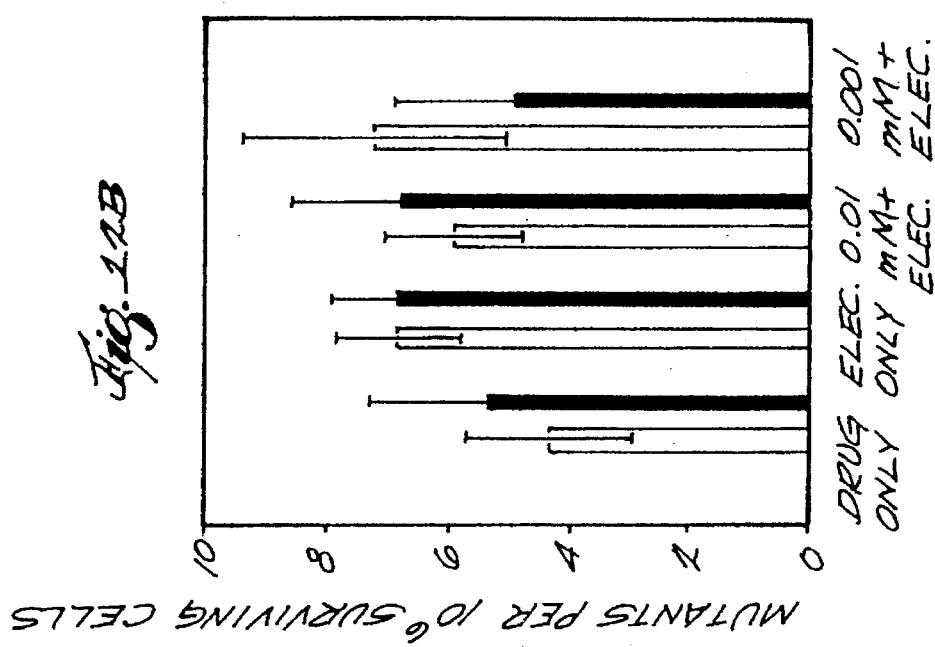
Figure 11A:
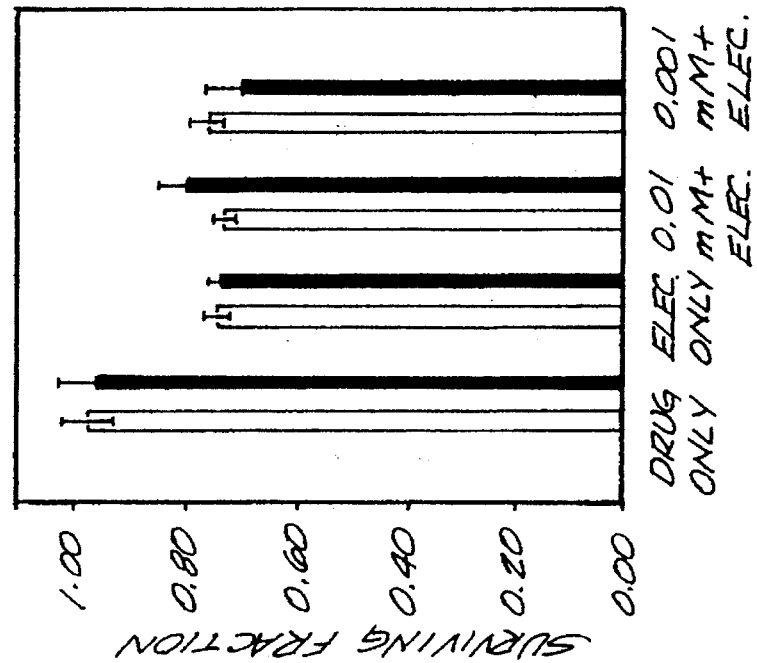
Figure 11D:
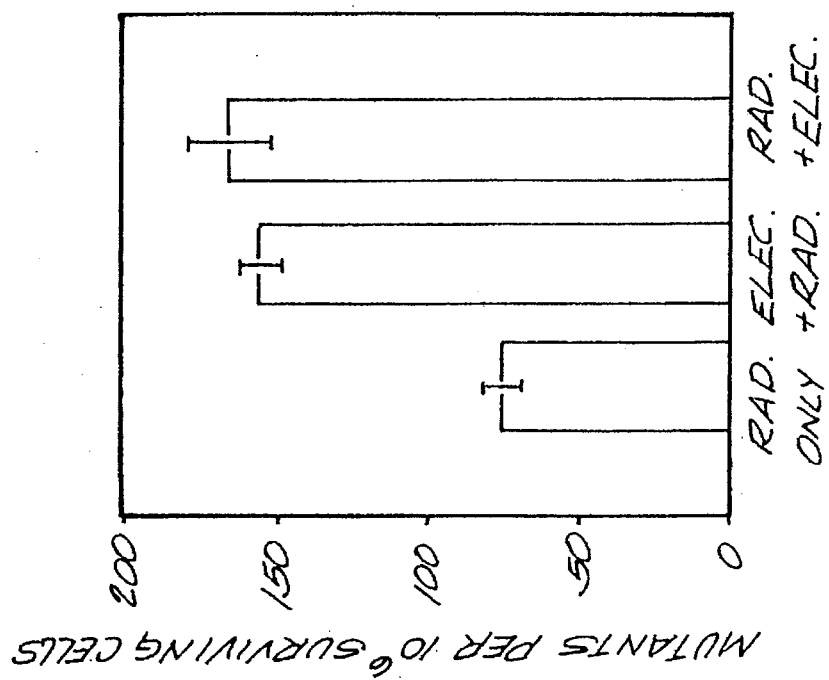
Figure 11C:
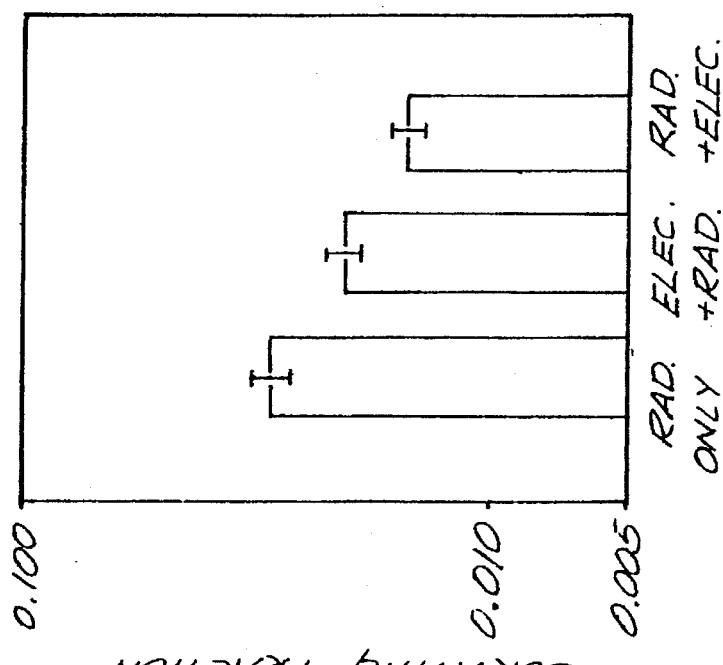

The anti-mutagenic effect of WR-2721 was demonstrated at the hprt locus in mice treated with cytoxan and cisplatin, FIGS. 11C and 11D, respectively. The reduction in mutant frequencies of T-lymphocytes isolated from mice so treated shows WR-2721 and its metabolites to be effective as an antimutagens against chemical as well as radiation insult.

II. Phosphorothioate Protection from Low Dosages.

The phosphorothioates and associated metabolites further achieve mutagen protection at very low concentrations, compared to concentrations required to protect against cell lethality. This conclusion is based on the observations that S-2-(3-aminopropylamino)ethyl phosphorothioic acid is equally antimutagenic at concentrations of 400 mg/kg, 200 mg/kg, 100 mg/kg, and 50 mg/kg (see FIG. 2, ref. 10). Mutant frequencies of T lymphocytes isolated from mice irradiated with 150 cGy of fission neutrons were $9.0 \times 10^{-5} \pm 1.2 \times 10^{-5}$ (1 standard error of the mean) for irradiated controls, $1.2 \times 10^{-5} \pm 1.0 \times 10^{-5}$ (S.E.) for 400 mg/kg, $7.8 \times 10^{-6} \pm 2.7 \times 10^{-6}$ (S.E.) for 200 mg/kg, $1.5 \times 10^{-5} \pm 1.4 \times 10^{-6}$ (S.E.) for 100 mg/kg, and $6.3 \times 10^{-6} \pm 3.2 \times 10^{-6}$ (S.E.) for 50 mg/kg. Under in vitro conditions, the free thiol form of S-2-(3-aminopropylamino)ethylphosphorothioic acid, i.e., 2-[(aminopropyl)amino]ethanethiol was administered as an antimutagen to cultured Chinese hamster ovary cells at a concentration range from 4 mM down to 0.01 mM. When administered 30 min prior to irradiation with 750 cGy of $^{60}$Co gamma rays (see FIG. 3), the drug and its metabolite is significantly effective as an antimutagen.

Administration of 2-[(aminopropyl)amino]ethanethiol also results in the formation of its disulfide. Protection against the cell killing effects of radiation by 2-[(aminopropyl)amino]ethanethiol rapidly diminishes as the concentration falls from 4 mM to 0.01 mM (see FIG. 4).

III. Disulfide Metabolite Mutagenic Protection.

The presence of disulfide metabolite of the phosphorothioate class of compounds corresponds to antimutagenic protection. This conclusion is based on the observations that, following the administration of 4 mM of 2-[(aminopropyl)amino]ethanethiol, protection against radiation-induced (i.e., fission neutrons) somatic mutations at the hypoxanthine-guanine phosphoribosyl transferase locus in Chinese hamster ovary cells correlates with the measured disulfide as compared to the free thiol (see FIG. 5).

Subsequent thiol and disulfide concentrations were measured by using monobromobiamine (mBBr), which reacts selectively with thiols via a Sn 2 displacement process to produce a fluorescent derivative. These methods were developed to specifically measure 2-[(aminopropyl)amino] ethanethiol, its phosphorothioate, and its disulfide. Chinese hamster ovary cells, $5 \times 10^6$ in 5 ml of growth medium, were administered 4 mM of 2-[(aminopropyl)amino]ethanethiol for 30 min at 37° C. They were then centrifuged, washed with a buffer, and resuspended in fresh medium up to an additional 4 h. After 15 min, 30 min, 1 h, 2 h, and 4 h of incubation, a sample of cells was removed and exposed to 150 cGy of fission neutrons. At these times various measurements made included: survival measurements, mutation measurements, and intracelluar measurements of 2-[(aminopropyl)amino]ethanethiol and its disulfide. The data contained in FIG. 5 demonstrate that survival protection is well correlated with thiol measurements. This is consistent with conventional understandings and teachings. The disulfide concentration was measured to be significantly less than that of the thiol, but the rate of its decrease with time was less than that found for the thiol. Measured protection against mutagenesis remained constant over this time range correlating with the kinetics of disulfide as opposed to the thiol concentration. The disulfide form of this thiol closely resembles the polyamine spermine (see FIG. 6). Polyamines are known to be involved in the repair of DNA damage due to ionizing and UV irradiation. The measurements indicate an inability to protect against radiation-induced lethality by the phosphorothioate class of chemicals and their associated metabolites when they are added after radiation. Coupling these data with the demonstrated ability to protect against radiation-induced mutagenesis under similar post radiation exposure conditions, make it clear that it is thus the fidelity, not the amount or quantity, of DNA damage which is being affected by these agents. This is also consistent with the properties of polyamines which have been shown to stabilize DNA against enzymatic degradation.

The prior art has indicated that the disulfide is not a protective metabolite of either the phosphorothioates or thiols. The instant data indicates however that the disulfide metabolite of the phosphorothioate is a protective moiety in preventing mutagen- (i.e., radiation) induced somatic mutations. The disulfide metabolite has a close similarity in structure and composition to polyamines, which are known endogenous agents capable of stabilizing chromatin and affecting DNA repair. Further, the phosphorothioates S-2-(3-aminopropylamino)ethyl (WR-2721), S-2-(4-aminobutylamino)ethyl (WR-2822), and S-2-(7-aminoheptylamino)ethyl have been shown in the prior art to competitively inhibit the uptake of the polyamine putrescine into rat lung tissue. The importance of the disulfide moiety in the post mutagen (i.e., radiation) exposure-protection process against the formation of somatic mutations demonstrates a surprising advantage for phosphorothioate compounds which form polyamine-like disulfides for use as antimutagenic chemopreventive agents.

The polyamine spermine and the disulfide WR-33278 are structurally similar agents capable of binding to DNA. As described above, WR-33278 is the disulfide metabolite of the S-2-(3-aminopropylamino)ethylphosphorothioic acid (WR-2721). Because of their reported structural and functional similarties, spermine and WR-33278 were compared with respect to cell survival and mutation induction at the hypoxanthine-guanine phosphoribosyl transferase (hprt) locus in Chinese hamster AA8 cells. Both WR-33278 and spermine were shown to be effective in protecting against radiation-induced mutagenesis, whether administered before or after irradiation.

In order to facilitate both the uptake of WR-33278 into cells and the direct comparison between the protective properties of WR-33278 and spermine, these agents (at concentrations of 0.01 mM and 0.001 mM) were electroporated into cells. Electroporation, 300 V and 125 μFD, was performed either 30 min prior to or 3 h following exposure of cells to 750 cGy ($^{60}$Co gamma rays) of ionizing radiation. Electroporation alone reduced cell survival to 75% but had no effect on hprt mutation frequency. (See FIGS. 12A and 12B.) The electroporation of either spermine or WR-33278 at concentrations greater than 0.01 mM was extremely toxic and, therefore, precluded the study of higher concentrations of these agents. The exposure of cells to both electroporation and irradiation gave rise to enhanced cell killing and mutation induction, with the sequence of irradiation followed 3 h later by electroporation being the more toxic protocol. Cell survival values at a radiation dose of 750 cGy were enhanced by factors of 1.3 and 1.8 following electroporation of 0.01 mM of spermine and WR-33278, respectively, 30 min prior to irradiation. Neither agent was protective at a concentration of 0.001 mM. See FIGS. 12C and 12D.)

Protection against radiation-induced hprt mutations was observed for both spermine and WR-33278 under all experimental conditions tested. Spermine at concentrations of 0.01 mM and 0.001 mM administered 30 min before or 3 h after irradiation reduced mutation frequencies by 2.2, 1.2, 1.9 and 2.2, respectively. WR-33278 at concentrations of 0.01 mM and 0.001 mM administered 30 min before or 3 h after irradiation lowered mutation frequencies by factors of 1.8, 1.3, 1.4 and 2.0, respectively.

The close agreement in the magnitudes of effect induced by spermine and WR-33278 against mutagenesis is consistent with their known structural and functional similarities. These data suggest that the properties of radioprotection and chemoprevention exhibited by the phosphorothioate (WR-2721) and associated aminothiol (WR-1065) and disulfide (WR-33278) metabolites may be mediated in part via endogenous polyamine-like processes. Such a mechanism has important implications with respect to the design and development of a new generation drugs for use in radioprotective and chemopreventive agents.

To determine what role, if any, is performed by the amine functionality in either the WR-2721, WR-1065, or WR-33278 anti-mutagens, the radiation survival, protection and anti-mutagenic properties of the aminothiols 1-cysteine and N-acetylcysteine were compared. As shown in FIGS. 12E–G, 1-cysteine is an effective radioprotector, rendered less effective when the amino group is acetylated (FIGS. 12E–F.) Protection against radiation-induced mutagenesis at the hprt locus in CHO AA8 cells is also adversely affected, further supporting the proposition that, at least in part, an amine functionality present in conjunction a phosphorothioate, thiol, or disulfide functionality may be responsible for protection against mutagenicity by WR-2721 and its metabolites.

IV. Phosphorothioate Protection Against Mutagenesis

The ability to protect against mutagen-induced somatic mutations is a general property of the phosphorothioates and their associated metabolites. This advantage demonstrated by the data obtained by experiments on cultured Chinese hamster ovary cells first exposed to 150 cGy of fission neutrons and then applying for 30 min a quantity of 4 mM of either 3-[(2-mercaptoethyl)amino]propionamide p-toluenesulfonate (WR-2529), S-1-(aminoethyl)phosphorothioic acid (WR-638), S-[2-(3-methylaminopropyl)aminoethyl] phosphorothioate acid (WR-3689), and S-1-(2-hydroxy-3-amino)propyl phosphorothioic acid (WR-77913) (see FIG. 8). All of these agents, including 2-[3-(methylamino)propylamino]ethanethiol (WR-255591) were effective anti-mutagens when they were added to cells at a concentration of 4 mM at about 30 min prior to exposure to fission neutrons (see FIG. 8).

Figure 9:
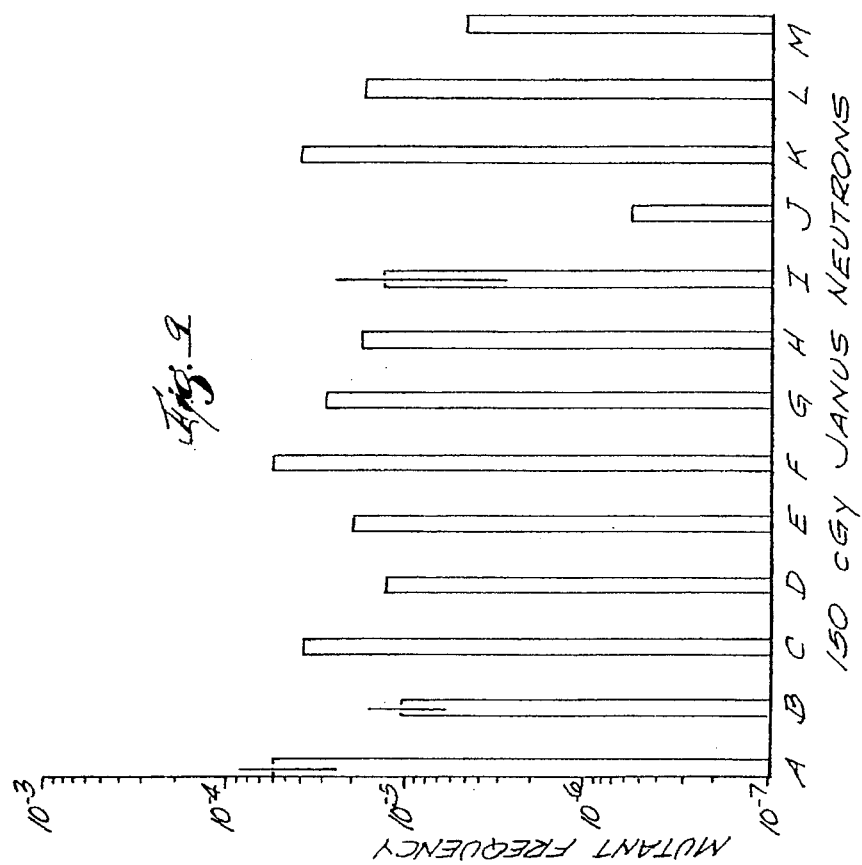

Protection against radiation-induced somatic mutations in mammals (i.e., mice) was also demonstrated for S-1-(aminoethyl)phosphorothioic acid (WR-638) under conditions in which a dose of 520 mg/kg was administered ip to animals within about 10 min after whole-body exposure to 750 cGy of $^{60}$Co gamma rays (see FIG. 9). Phosphorothioates exhibited antimutagenic properties in mammals when administered 30 min prior to exposure to 750 cGy of $^{60}$Co gamma rays. The phosphorothioates included S-[2-(3-methylaminopropyl)aminoethyl]phosphorothioate acid (WR-3689), and S-2-(4-aminobutylamino)ethylphosphorothioic acid (WR-2822). These data demonstrate that the antimutagenic properties of S-2-(3-aminopropylamino)ethylphosphorothioic acid (WR-2721) are also observable in selected ones of the phosphorothioates and their associated metabolites.

While preferred embodiments of the invention have been shown and described, it will be clear to those skilled in the art that various changes and modifications can be made without departing from the invention in its broader aspects as set forth in the claims provided hereinafter.

What is claimed is:

1. A method for reducing mammal cell mutations induced by irradiation, comprising the steps of:
   (a) preparing a dosage of a chemical compound selected from the group consisting of an aminoalkylphosphorothioate and an associated amino aminoalkylphoshorothioate metabolite, said dosage from an effective amount to less then 50 mg/kg of mammal body weight; and
   (b) administering said dosage to the mammal before irradiation of the mammal.

2. The method as defined in claim 1 wherein said dosage is less than about 25 mg/kg mammal weight.

3. The method as defined in claim 1 wherein said phosphorothioate and metabolite is selected from the group consisting of S-1-(aminoethyl)phosphorothioic acid (WR-638), S-[2-(3-methylaminopropyl)aminoethyl]phosphorothioate acid (WR-3689), S-2-(4-aminobutylamino)ethylphosphorothioic acid (WR-2822), 3-[(2-mercapto ethyl)amino]propionamide p-toluenesulfonate (WR-2529), S-1-(2-hydroxy-3-amino)propyl phosphorothioic acid (WR-77913), 2-[3-(methylamino) propylamino]ethanethiol (WR-255591), S-2-(5-aminopentylamino)ethyl phosphorothioic acid (WR-2823), and 1-[3-(3-aminopropyl)thiazolidin-2-Y1]-D-gluco-1,2,3,4,5 pentane-pentol dihydrochloride (WR-255709).

4. The method as defined in claim 1 wherein the irradiation is fast neutrons.

5. The method as defined in claim 1 wherein said dosage is administered about thirty minutes prior to the irradiation of the mammal.

6. A method for reducing mammal cell mutations induced by irradiation, comprising the steps of:
   (a) preparing a dosage of a metabolite of an aminoalkylphosphorothioate compound, said dosage from an effective amount to less than 50 mg/kg of mammal body weight; and
   (b) administering said dosage to the mammal at a time prior to the irradiation.

7. The method as defined in claim 6 wherein said metabolite forms a polyamine compound when administered to the mammal.

8. The method as defined in claim 6 wherein said metabolite of said aminoalkylphosphorothioate compound is [2-[(aminopropyl)amino]ethanethiol]N,N,'-dithiodi-2,1-(ethanediyl)bis-1,3-propanediamine (WR-33278).

9. The method as defined in claim 6 wherein said phosphorothioate compound is selected from the group consisting of S-1-(aminoethyl)phosphorothioic acid (WR-638), S-[2-(3-methylaminopropyl)aminoethyl]phosphorothioate acid (WR-3689), S-2-(4-aminobutylamino)ethylphosphorothioic acid (WR-2822), 3-[(2-mercapto ethyl)amino]propionamide p-toluenesulfonate (WR-2529), S-1-(2-hydroxy-3-amino) propyl phosphorothioic acid (WR-77913), 2-[3-(methylamino) propylamino]ethanethiol (WR-255591), S-2-(5-aminopentylamino)ethyl phosphorothioic acid (WR-2823), and 1-[3-(3-aminopropyl)thiazolidin- 2-Y1]-D-gluco-1,2,3,4,5 pentane-pentol dihydrochloride (WR-255709).

10. The method as defined in claim 6 wherein said dosage is administered about 30 minutes before irradiation.

11. The method as defined in claim 1 wherein said chemical compound is an aminoalkylphosphorothioate which forms a polyamine disulfide under conditions of cellular metabolism.

* * * * *

UNITED STATES PATENT AND TRADEMARK OFFICE
CERTIFICATE OF CORRECTION

PATENT NO.    :   5,567,686

DATED         :   October 22, 1996

INVENTOR(S)   :   David J. Grdina

It is certified that error appears in the above-identified patent and that said Letters Patent is hereby corrected as shown below:

Column 1, line 5, insert the following:

--This invention was made with Government Support under Contract No. W-31-109-ENG-38 between the University of Chicago and the U.S. Department of Energy. The Government has certain rights in this invention.--

Signed and Sealed this

Twenty-seventh Day of May, 1997

*Attest:*

BRUCE LEHMAN

*Attesting Officer*  Commissioner of Patents and Trademarks